(12) United States Patent
Nielsen et al.

(10) Patent No.: US 8,420,378 B2
(45) Date of Patent: Apr. 16, 2013

(54) DNA ENCODING PROTEIN AND METHODS OF USING SAME

(75) Inventors: Jens Bredal Nielsen, Göteborg (SE); Torsten Ulrik Bak Regueira, Copenhagen S (DK)

(73) Assignee: Danmarks Tekniske Universitet, Lyngby (DK)

( * ) Notice: Subject to any disclaimer, the term of this patent is extended or adjusted under 35 U.S.C. 154(b) by 266 days.

(21) Appl. No.: 12/663,773

(22) PCT Filed: Jun. 12, 2008

(86) PCT No.: PCT/DK2008/050138
§ 371 (c)(1),
(2), (4) Date: Apr. 1, 2010

(87) PCT Pub. No.: WO2008/151636
PCT Pub. Date: Dec. 18, 2008

(65) Prior Publication Data
US 2010/0190238 A1 Jul. 29, 2010

Related U.S. Application Data

(60) Provisional application No. 60/943,932, filed on Jun. 14, 2007.

(30) Foreign Application Priority Data

Jun. 14, 2007 (EP) .................................. 07110287

(51) Int. Cl.
*C12N 1/15* (2006.01)

(52) U.S. Cl.
USPC ................... 435/254.5; 435/320.1; 435/69.1; 536/23.1; 530/350

(58) Field of Classification Search ........................ None
See application file for complete search history.

(56) References Cited

PUBLICATIONS

"IMP dehydrogenase/GMP reductase" from Aspergillus oryzae; Database Uniprot Consortium [Online]; Jan. 24, 2006, XP-002442716, Database accession No. Q2U613.

*Primary Examiner* — Hope Robinson
(74) *Attorney, Agent, or Firm* — Knobbe Martens Olson & Bear LLP

(57) ABSTRACT

The present invention relates to novel tools for improving MPA production. In particular, the present invention relates to fungal enzymes that are specific for MPA synthesis.

22 Claims, 10 Drawing Sheets

DNA ENCODING PROTEIN AND METHODS OF USING SAME

CROSS-REFERENCE TO RELATED APPLICATIONS

This application claims the benefit and priority to and is a U.S. National Phase Application of PCT International Application Number PCT/DK2008/050138, filed on Jun. 12, 2008, designating the United States of America and published in the English language, which is an International Application of and claims the benefit of priority to European Patent Application No. EP 07110287.5, filed on Jun. 14, 2007, and U.S. Provisional Application No. 60/943,932, filed on Jun. 14, 2007. The disclosures of the above-referenced applications are hereby expressly incorporated by reference in their entireties.

SEQUENCE LISTING IN ELECTRONIC FORMAT

The present application is being filed along with a Sequence Listing in electronic format. The Sequence Listing was updated by a file entitled 2012_10_01_Sequence_PLOUG39_004APC.txt, created on Sep. 27, 2012, modified on Oct. 1, 2012 which is 75,654 bytes in size. The information in the electronic format of the Sequence Listing is incorporated herein by reference in its entirety.

TECHNICAL FIELD OF THE INVENTION

The present invention relates to the field of fungal secondary metabolites. In particular the present invention relates to enzymes involved in the synthesis of mycophenolic acid (MPA).

BACKGROUND OF THE INVENTION

Mycophenolic acid (MPA) is a natural compound produced by some fungi, mainly of the *Pencicillum* fungus species. MPA has a wealth of applications; the most important application at present being a key drug in the treatment of organ transplanted patients. MPA was first discovered in 1893 and has been investigated thoroughly since its discovery. However, despite the importance of this drug, no information is available about the enzymes responsible for MPA synthesis in the fungus. On an industrial scale, MPA is thus currently produced by relatively laborious and inefficient fermentation processes of the natural fungus, primarily *Penicillium brevicompactum*.

Hence, there exists a need in the art for improved methods for producing MPA. Furthermore, it is likely that new commercial applications of MPA, and thereby an increased demand for the compound, will result from cheaper and more efficient production methods.

SUMMARY OF THE INVENTION

Thus, an object of the present invention relates to the isolation of the genes encoding the enzymes involved in the production of MPA.

In a first aspect, the present invention thus relates to an expression vector comprising at least one polynucleotide sequence encoding an polypeptide, wherein said polypeptide is selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8, and wherein said polypeptide(s) have a sequence identity of at least 70% with the sequence(s) set forth in SEQ ID NOs 1-5, and 7-8, and wherein said polypeptide has a sequence identity of at least 90% with the sequence set forth in SEQ ID NO: 6. SEQ ID NOs 1-8 encode enzymes involved in the MPA synthesis in the *P. brevicompactum* fungus.

In further aspects, the present invention relates to host cells comprising the vector according to the invention as well as methods for cultivating such host cells in order to produce MPA.

In yet further aspects, the present invention relates to:
i) an isolated polynucleotide sequence encoding a polypeptide with 80-100% identity with SEQ ID NO: 1,
ii) an isolated polynucleotide sequence encoding a polypeptide with 80-100% identity with SEQ ID NO: 2,
iii) an isolated polynucleotide sequence encoding a polypeptide with 80-100% identity with SEQ ID NO: 3,
iv) an isolated polynucleotide sequence encoding a polypeptide with 80-100% identity with SEQ ID NO: 4,
v) an isolated polynucleotide sequence encoding a polypeptide with 80-100% identity with SEQ ID NO: 5,
vi) an isolated polynucleotide sequence encoding a polypeptide with 90-100% identity with SEQ ID NO: 6,
vii) an isolated polynucleotide sequence encoding a polypeptide with 80-100% identity with SEQ ID NO: 7,
viii) an isolated polynucleotide sequence encoding a polypeptide with 80-100% identity with SEQ ID NO: 8, and
ix) a polypeptide encoded by any one of these polynucleotide sequences.

A final aspect relates to use of host cells according to the present invention for production of MPA.

DETAILED DESCRIPTION OF THE INVENTION

The Italian physician, Bartolomeo Gosio discovered the antibiotic effect of mycophenolic acid (MPA) in 1893 by observing that the anthrax *bacillus* was inhibited by one of his purified fungal metabolites from *Penicillium brevicompactum*. Interestingly, MPA was thereby the first antibiotic to be crystallised from a living organism, and since Gosio's discovery more than 100 years ago, MPA has turned out to be a "miracle drug". It has been used as an immunosuppressant in kidney, heart and liver transplantations and has been reported to possess antiviral, antifungal, antibacterial, antitumor, and anti-psoriasis activities.

Analyses by Birch et al. 1957 showed that MPA belongs to the group of compounds named meroterpenoids. Meroterpenoids are compounds which consist of a polyketide fused to a mevalonate pathway intermediate. MPA consists of a polyketide fused to farnesyl diphosphate, the latter being derived from the mevalonate pathway. Thus two distinct pathways are involved in the production of MPA.

Several *Penicillium* spp. are capable of producing MPA, and due to its fundamental biological activities great interest has been dedicated to the elucidation of the structure, the biosynthesis and the mechanism behind its promising biological properties. Fungal production of MPA has been shown in the following *Penicillium* species: *P. brevicompactum, P. stoloniferum, P. scabrum, P. nagemi, P. szaferi, P. patris-mei, P. griscobrunneum, P. viridicatum, P. carneum, P. arenicola, P. echinulatum, P. verrucosum,* and *P. brunneo-stoloniferum*. In addition, the fungus *Byssochlamys nivea* has also been reported to produce MPA.

Even though it is known that it is more than likely that a polyketide synthase (PKS) is involved in the MPA synthesis and even though most PKS proteins share conserved regions, it was not possible to design PKS primers that allowed cloning of MPA PKS in *P. brevicompactum*. The explanation most likely being that the structural diversity produced by fungal PKSs is enormous combined with the fact that the fungus furthermore encodes a large number of different PKS enzymes responsible for production of a large number of polyketides (MPA being a polyketide). Furthermore, the structure of MPA indicates that the MPA PKS should belong to a non-reducing type with methyl transferase activity, which thus far did not contain any characterized PKS enzymes. There was therefore reason to believe that the MPA PKS would differ in sequence from other known PKS enzymes.

The structure of MPA (formula I) is shown below:

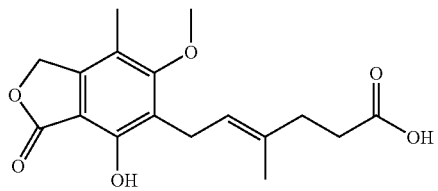

(I)

The IUPAC name of MPA is: (E)-6-(4-hydroxy-6-methoxy-7-methyl-3-oxo-1,3-dihydroisobenzofuran-5-yl)-4-methylhex-4-enoic acid.

MPA inhibits Inosine Monophosphate Dehydrogenase (IMPDH) (EC 1.1.1.205). IMPDH is an important enzyme in the de novo biosynthesis of GMP, catalyzing the nicotinamide adenine dinucleotide (NAD) dependent oxidation of IMP to xanthosine-5-monophosphate (XMP). Since GMP is one of the building blocks of DNA, IMP dehydrogenase is an obvious target for drugs intended for DNA biosynthesis inhibition, such as anti-cancer agents. There are two GMP producing pathways: (i) the "de novo pathway", where IMP is a key-intermediate; and (ii) the "salvage pathway" in which free purines are formed in catabolic processes and reconverted to nucleoside monophosphates by reacting with 5-phospho-α-D-ribofuranosyl diphosphate.

MPA inhibits the proliferation of lymphocytes, because they are almost entirely dependent on the de novo GMP biosynthesis pathway. Cancer cell lines are however, less sensitive to MPA as they are capable of obtaining GMP via both the de novo pathway and the salvage pathway.

IMPDH proteins from approximately 125 different organisms have thus far been isolated and they show a high degree of similarity. Some organisms contain more than one gene encoding putative IMPDH proteins. Unpublished blast searches performed by the inventors in connection with the present invention revealed that fungal genomes closely related to *P. brevicompactum* (*Aspergillus oryzae*, *Aspergillus terreus*, *Magnaporthe grisea* and *Neurospora crassa*) contain only one copy of the IMPDH gene. No IMPDH sequences from *P. brevicompactum* have thus far been reported.

It has previously been shown that an MPA resistant strain of *Candida albicans* is resistant to high titers of MPA due to over expression of the IMPDH gene. In connection with the present invention it was a crucial step to realize that a similar natural mechanism in *P. brevicompactum* is rendering this fungus MPA resistant—the *P. brevicompactum* genome encodes two IMPDH genes.

It was presumed that the enzymes responsible for MPA synthesis would be present in a gene cluster in the genome of the *P. brevicompactum* fungus since it has previously been reported that many naturally occurring polyketides are produced by enzymes that are all present within a specific gene cluster.

The inventors succeeded in identifying the MPA biosynthesis gene cluster in *P. brevicompactum* by screening the genome for IMPDH genes by the use of a BAC library as described in the Examples.

In a first aspect, the present invention thus relates to an expression vector comprising at least one polynucleotide sequence encoding a polypeptide, wherein said polypeptide is selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8, and wherein said polypeptide(s) have a sequence identity of at least 70% with the sequence(s) set forth in SEQ ID NOs 1-5, and 7-8, and wherein said polypeptide has a sequence identity of at least 90% with the sequence set forth in SEQ ID NO: 6. SEQ ID NOs 1-8 encode enzymes involved in the MPA synthesis in the *P. brevicompactum* fungus. In the fungus, the genes encoding these eight polypeptides are present in a gene cluster.

It is understood that the term "an expression vector" also covers the situation where the selected sequences are inserted into two or more expression vectors.

In a preferred embodiment, one or more expression vectors encode at least two of the said polypeptides, more preferably at least three, even more preferably at least four, even more preferably at least five, even more preferably at least six, even more preferably at least seven, and most preferably eight polypeptides.

Likewise, the present invention relates to host cells comprising such vectors. The host cell may be any cell that can be grown in culture such as bacteria, mammalian cells, fungal cells, plant cells, etc. However, as it appears that some polypeptides are post-translationally processed, it is preferred to use eukaryotic host cells. It is even more preferred to use fungal cells such as e.g. a yeast cell or a fungus that naturally produces MPA. Yeast cells have the advantage of being relatively easy to ferment in a large scale and yeasts may thus be a practical host cell for many applications.

It follows that the invention furthermore relates to a method of cultivating a host cell according to the present invention, wherein said method comprises growing the cell in a growth media under appropriate conditions. In a preferred embodiment, the method further comprises the step of recovering and optionally purifying MPA.

In yet further aspects, the present invention relates to:
i) An isolated polynucleotide sequence encoding a polypeptide with 70-100%, preferably 80-100, and most preferably 90-100% identity with SEQ ID NO: 1. SEQ ID NO: 1 corresponds to the polypeptide encoded by mpaA. mpaA encodes a polypeptide with the characteristics of a prenyl transferase. In a preferred embodiment, the conserved areas in the encoded polypeptide have a degree of identity of at least 80%, preferably at least 90%, and most preferably at least 95% identity with the corresponding conserved areas in SEQ ID NO: 1.
ii) An isolated polynucleotide sequence encoding a polypeptide with 70-100% identity, preferably 80-100%, and most preferably 90-100% identity with SEQ ID NO: 2. SEQ ID NO: 2 corresponds to the polypeptide encoded by mpaB and which is a polypeptide with unknown activity, but it is most likely involved in MPA biosynthesis.
iii) An isolated polynucleotide sequence encoding a polypeptide with 70-100%, preferably 80-100, and most preferably 90-100% identity with SEQ ID NO: 3. SEQ ID NO: 3 corresponds to the polypeptide encoded by mpaC—a putative polyketide synthase (PKS). In a preferred embodiment, the conserved areas in the encoded polypeptide have a degree of identity of at least 80%, preferably at least 90%, and most preferably at least 95% identity with the corresponding conserved areas in SEQ ID NO: 3.

iv) An isolated polynucleotide sequence encoding a polypeptide with 70-100%, preferably 80-100, and most preferably 90-100% identity with SEQ ID NO: 4. SEQ ID NO: 4 corresponds to the polypeptide encoded by mpaD—a putative p450 monooxygenase). In a preferred embodiment, the conserved areas in the encoded polypeptide have a degree of identity of at least 80%, preferably at least 90%, and most preferably at least 95% identity with the corresponding conserved areas in SEQ ID NO: 4.

v) An isolated polynucleotide sequence encoding a polypeptide with 70-100%, preferably 80-100%, and most preferably 90-100% identity with SEQ ID NO: 5. SEQ ID NO: 5 corresponds to the polypeptide encoded by mpaE—a putative Zn dependent hydrolase. In a preferred embodiment, the conserved areas in the encoded polypeptide have a degree of identity of at least 80%, preferably at least 90%, and most preferably at least 95% identity with the corresponding conserved areas in SEQ ID NO: 5.

vi) An isolated polynucleotide sequence encoding a polypeptide with 90-100%, preferably 95-100% identity with SEQ ID NO: 6. SEQ ID NO: 6 corresponds to the polypeptide encoded by mpaF—a putative IMPDH. In a preferred embodiment, the conserved areas in the encoded polypeptide have a degree of identity of at least 90% preferably at least 95% identity with the corresponding conserved areas in SEQ ID NO: 6.

vii) An isolated polynucleotide sequence encoding a polypeptide with 70-100%, preferably 80-100%, and most preferably 90-100% identity with SEQ ID NO: 7. SEQ ID NO: 7 corresponds to mpaG—a putative O-methyltransferase. In a preferred embodiment, the conserved areas in the encoded polypeptide have a degree of identity of at least 80%, preferably at least 90%, most preferably at least 95% identity with the corresponding conserved areas in SEQ ID NO: 7.

viii) An isolated polynucleotide sequence encoding a polypeptide with 70-100%, preferably 80-100%, and most preferably 90-100% identity with SEQ ID NO: 8. SEQ ID NO: 8 corresponds to mpaH—a putative hydrolase. In a preferred embodiment, the conserved areas in the encoded polypeptide have a degree of identity of at least 80%, preferably at least 90%, most preferably at least 95% identity with the corresponding conserved areas in SEQ ID NO: 8.

It follows that the present invention furthermore relates to polypeptides encoded by any one of these polynucleotide sequences. Furthermore, the polypeptide may be a fragment thereof, wherein said fragment has a length of at least 100, preferably 150, more preferably 200, more preferably 250, and most preferably 300 amino acids.

Finally, the invention relates to the use of a host cell according to the invention for production of MPA.

It should be noted that embodiments and features described in the context of one of the aspects of the present invention also apply to the other aspects of the invention.

The invention will now be described in further details in the following non-limiting examples.

BRIEF DESCRIPTION OF THE FIGURES

FIG. 3: Alignment of MT domains from various polyketide synthases (MlcA, MlcB, LNKS, LDKS, and mpaC). mpaC (SEQ ID NO: 3) from the *P. brevicompactum* MPA biosynthesis gene cluster contains three conserved motifs (Motif I in MpaC: ILEIGAGTG (SEQ ID NO: 33); motif II in MpaC: GQYDIVLS (SEQ ID NO: 34); motif III in MpaC: LLRPDGILC (SEQ ID NO: 35)). These motifs are known to be present in most PKS MT domains. The presence of an MT domain is consistent with the fact that methylation occurs at the tetraketide stage of the MPA biosynthesis.

FIG. 6: Alignment of *P. brevicompactum* MpaG to related O-methyltransferase proteins.

PCR analysis results amplified from genomic DNA of the wild-type and some transformants. A) Amplified upstream mpaC and upstream 2/3 HygR cassette using primers KO-MpaC-F1 (SEQ ID NO: 29) and Upst-HygR-N (SEQ ID NO: 26). B) Amplified downstream 2/3 HygR cassette and downstream mpaC using primers Dwst-HygF-N (SEQ ID NO: 27) and KO-MpaC-Re3 (SEQ ID NO: 30). The PCR product size expected from the deletion stains for A) and B) are 4.5 and 4.4 kb, respectively. For the wild-type or transformants carrying non-homologous recombination, no PCR product is expected. C) Amplified 1/3 of mpaC gene using primers KO-2 mpaC-UF (SEQ ID NO: 31) and KO-2 mpaC-URa (SEQ ID NO: 32). The expected PCR product for the wild-type strain is 2.6 kb, whereas no PCR product is expected for the deletion strains.

Figure 10:
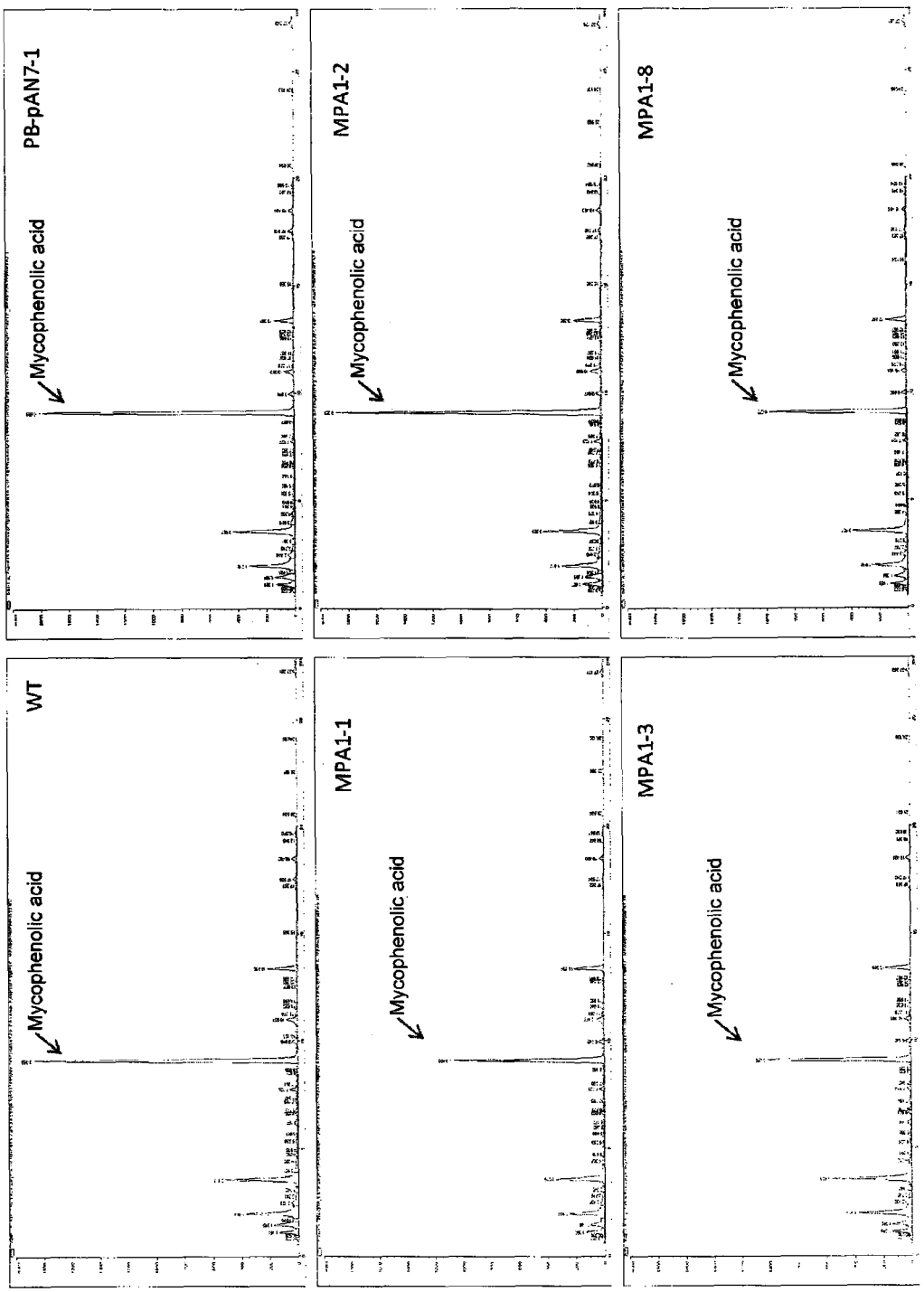

FIG. 10: The following abbreviations are used in the figure: WT, the wild-type strain IBT23078; PB-pAN7-1, IBT23078 transformed with pAN7-1 plasmid; MPA1-1, MPA1-3 and MPA1-8, mpaC deletion strains; MPA1-2, IBT23078 contained random integrated of HygB cassette.

HPLC profiles of the reference and some transformants. All strains are grown on YES agar at 25° C. for 5 days. All chromatogram are illustrated at the same scale.

Figure 11:
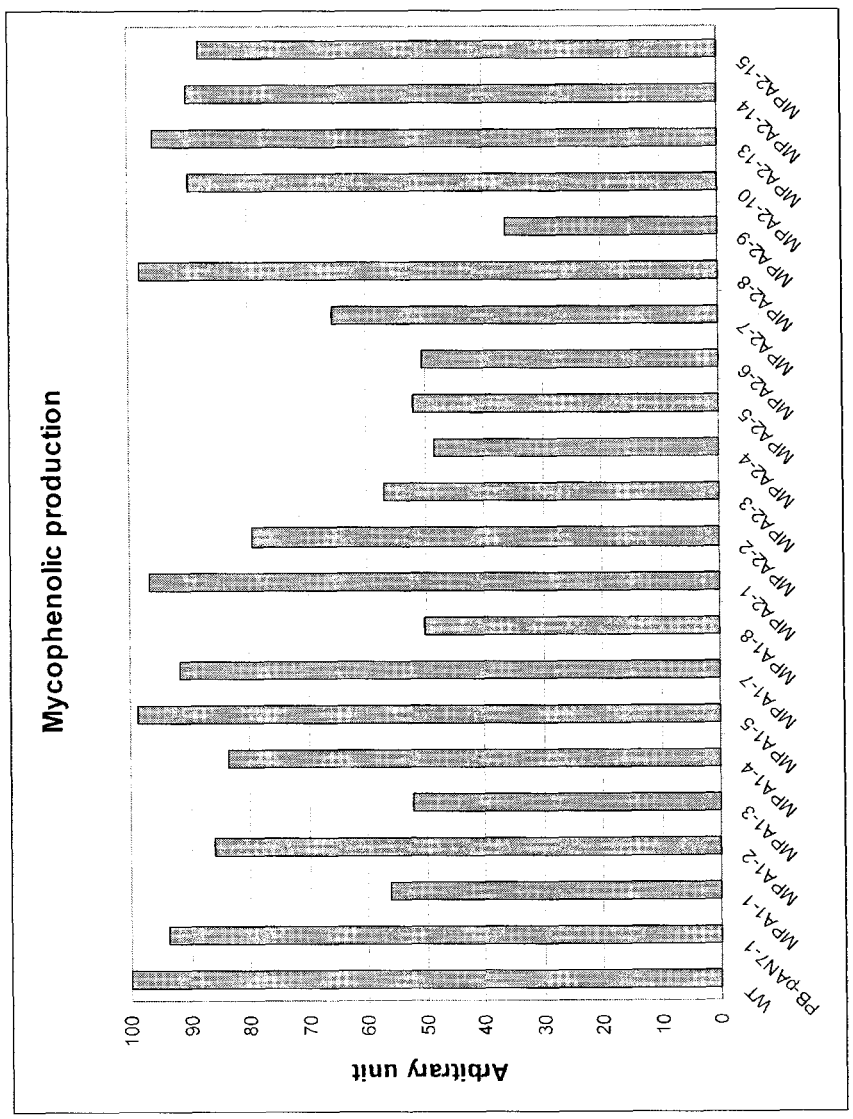

FIG. 11: The following abbreviations are used in the figure: WT, the wild-type strain IBT23078; PB-pAN7-1, transformant contained pAN7-1 plasmid; MPA1-and MPA2-series, transformants derived by bipartite method.

Mycophenolic acid production by wild-type and transformants grown on YES agar at 25° C. for 5 days. Data represents the relative amount of mycophenolic acid produced by transformants compared to the wild-type.

DEFINITIONS

Prior to discussing the present invention in further details, the following terms and conventions will first be defined:

Polyketides: Polyketides are secondary metabolites from bacteria, fungi, plants, and animals. Polyketides are derived from the polymerization of acetyl and propionyl subunits in a similar process to fatty acid synthesis catalyzed by polyketide synthases (PKSs). Polyketides also serve as building blocks for a broad range of natural products. Polyketides are structurally a very diverse family of natural products with an extremely broad range of biological activities and pharmacological properties. Polyketide antibiotics, antifungals, cytostatics, anticholesterolemics, antiparasitics, coccidiostatics, animal growth promotants and natural insecticides are in commercial use. MPA is classified as a polyketide with an attached farnesyl side chain—an intermediate from the mevalonate pathway (MPA may furthermore be classified as a meroterpenoid). Other examples of polyketides of great commercial and therpeutical interest are the cholesterol lowering statins such as e.g. lovastatin, atorvastatin, etc. Many naturally occurring polyketides are produced by enzymes that are all present within a specific gene cluster.

Gene cluster: The term "gene cluster" indicates that a specific number of genes involved in a biosynthetic pathway are localized closely to each other in the genome and that there is a first gene and a last gene that define the physical outer boundaries of the cluster.

Growth medium: The growth medium may be solid, semisolid or liquid and preferably contains an energy source as well as the required minerals (P, K, S, N, etc.).

Suitable incubation conditions: Preferred incubation conditions may vary depending on the host cell system. Some host cells may prefer mainly anaerobic conditions and other may prefer mainly aerobic conditions. All host cell systems prefer moist conditions, i.e. a water content in the media from 5-99%, preferably 10-90%, more preferably 20-80%, more preferably 30-70%, and most preferably 50-60%. Many host cell systems furthermore require continuous shaking. The incubation time may vary from less than 1 day to about a month, preferably 2-20 days, more preferably 4-15 days and most preferably 1-2 weeks.

Host cell: The term "host cells," denote, for example, micro-organisms, insect cells, and mammalian cells, which can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. Specific examples of mammalian cells and insect cells include human-derived cells, mouse-derived cells, fly-derived cells, silk worm-derived cells, and the like. Also, microorganisms such as *Escherichia coli* and yeast may be used.

Yeast: Yeasts include e.g. the following genera *Candida, Kluyveromyces, Pichia, Saccharomyces, Schizosaccharomyces, Yarrowia, Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* or *Trichoderma*. *Saccharomyces* species include *S. carlsbergensis, S. cerevisiae, S. diastaticus, S. douglasii, S. kluyveri, S. norbensis,* and *S. oviformiss*. *Aspergillus* species include *A. aculeatus, A. awamori, A. foetidus, A. japonicus, A. nidulans, A. niger, A. terreus* (the genome has been sequenced), *A. flavus* (the genome has been sequenced), *A. fumigatus* (the genome has been sequenced), and *A. oryzae*. *Fusarium* species include *F. bactridioides, F. cerealis, F. crookwellense, F. culmorum, F. graminearum, F. graminum, F. heterosporum, F. negundi, F. oxysporum, F. reticulatum, F. roseum, F. sambucinum, F. sarcochroum, F. sporotrichioides, F. sulphureum, F. torulosum, F. trichothecioides,* and *F. venenatum*. Other yeast species include e.g. *Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* and *Trichoderma viride*.

Promoter: The terms "promoter", "promoter region" or "promoter sequence" refer generally to transcriptional regulatory regions of a gene, which may be found at the 5' or 3' side of the coding region, or within the coding region, or within introns. As used herein the term promoter shall include any portion of genomic DNA (including genomic DNA disclosed herein), which is capable of initiating transcription of nucleotide sequences at levels detectable above background. Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Aspergillus nidulans* glyceraldehyde 3-phosphate dehydrogenase (gpdA) and *Fusarium oxysporum* trypsin-like protease, as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. It follows that the endogenous promoters may likewise be employed.

Expression vector: A vector is a component or composition for facilitating cell transduction or transfection by a selected nucleic acid, or expression of the nucleic acid in the cell. Vectors include, e.g., plasmids, cosmids, viruses, BACs, PACs, P1, YACs, bacteria, poly-lysine, as well as linear nucleotide fragments etc. An "expression vector" is a nucleic acid construct or sequence, generated recombinantly or synthetically, with a series of specific nucleic acid elements that permit transcription of a particular nucleic acid sequence in a host cell. The expression vector can be part of a plasmid, virus, or nucleic acid fragment. The expression vector typically includes a nucleic acid to be transcribed operably linked to a promoter. The nucleic acid to be transcribed is typically under the direction or control of the promoter. The expression vector may replicate autonomously in the host cell or may integrate into the host genome after the transfection or transduction and replicate as part of the genome.

Sequence identity: The term "sequence identity" is a measure of the degree of identity between polynucleotide sequences on a nucleotide-by-nucleotide basis or amino acid-by-amino acid basis, respectively) over a window of comparison.

EXAMPLES

Example 1

P. brevicompactum BAC Library

P. brevicompactum, strain IBT 23078, was obtained from the strain collection at Center for Microbial Biotechnology at the Technical University of Denmark. Chromosomal DNA was extracted from this strain. Amplicon Express subsequently constructed a 10 fold coverage BAC library on basis of the chromosomal P. brevicompactum DNA (PBBAC). The total number of clones in the library was 3,072.

Example 2

Screening of PBBAC Using IMPDH Primers

A first approach in the attempt of isolating the MPA gene cluster was to screen the library for PKS enzymes using degenerated primers designed on basis of various conserved PKS domains. Several PKS gene fragments from genomic DNA were amplified with these primers and sequenced. However, based on alignments none of these gene fragments belonged to the non-reducing PKS with methyltransferase activity, as needed for MPA PKS. Hence, the gene fragments could not be used as probes for MPA PKS in PBBAC.

The second approach was to find out if P. brevicompactum encodes more than one IMPDH gene and if that was the case, then hopefully the MPA gene cluster could be found as neighbouring sequences to one of these IMPDH gene copies. The background for this hypothesis being that the extra IMPDH gene copy may be the prerequisite for the existence of an enzymatic pathway that leads to synthesis of a compound (MPA) that inhibits the very activity of IMPDH. Perhaps this possible coexistence is reflected by the genomic structure resulting in a close physical proximity of the MPA gene cluster and the extra copy of the IMPDH gene.

IMPDH is a highly conserved protein and degenerate IMPDH primers were designed on basis of conserved domains of the protein. The IMPDH primers that were used for amplification of MPA cluster specific probes are shown in table 1 below:

TABLE 1

Degenerate IMPDH gene primers.

| Name | Sequence (degeneracy) |
|---|---|
| IMP_FW[a] | G G L T Y N D [F] |
| IMP_FW[b,c] | GGI GGI YTI ACT TAY AAY GAY TT (16)c |
| IMP_RV[a] | G N V V T R E Q A [A] |
| IMP_RV[b,c] | GC IGC YTG YTC ICK IGT IAC IAC RTT ICC (16) |

[a] amino acid sequence
[b] Letters in bold indicate degenerate nucleotides using the standard letter code.
[c] Inosine was used as a non-degenerate nucleotide analogue in order to reduce the redundancy.

A 1115 bp amplification product was obtained with the IMP_FW/RV primers. This fragment was used as a probe to screen the PBBAC library.

As the coverage of the PBBAC library was about 10 fold, a single copy of the IMPDH gene should yield approximately 10 hybridization signals, and two copies of the IMPDH gene would result in approximately 20 hybridization signals. Extensive experiments indeed indicated the existence of two IMPDH genes in P. brevicompactum genome, as 24 hybridization signals were found. This observation strongly indicated that P. brevicompactum obtained resistance against MPA by having an extra copy of the IMPDH gene. This mechanism (overexpression of IMPDH) is similar to the MPA resistance mechanism observed in Candida albicans.

The following five IMPDH BACs were selected for further analyses: 1-B12, 1-E13, 1-C23, 1-B16, 1-H11, and 1-I3. Depending on the hybridization pattern, these clones could be subdivided into the following groups:

a) 1-B12, 1-B16, 1-H11, and
b) 1-E13 and 1-C23

Sequence and blast analysis revealed that the neighbouring sequence in group a) was a ras GTPase activating protein. In connection with the present invention, the inventors had used blast searches of available fungal genomes to establish the number of IPMDH genes. They found that only one IMPDH gene was present in these organisms. Further blast searches revealed that IMPDH was located in close proximity to ras GTPase activator protein in Neurospora crassa, Magnaporthe grisea, A. oryzae, and A. terreus). This result indicated that the group a) BACs encoded the "standard" IMPDH gene in P. brevicompactum.

It was thus hypothesized that the group b) clones would encode the extra IMPDH copy that would hopefully be located in the MPA gene cluster or close to it. However, initial sequence analysis of the b) clones did not succeed—probably due to the large size of the clone.

Example 3

Sequencing of the MPA Gene Cluster

The process of sequencing the BAC clones suspected to contain the MPA gene cluster was outsourced to MWG Biotech. The company constructed a shotgun library of the BAC with an average insert size of app. 2-3 kb followed by random picking of a number of clones for end-sequencing. The size of the BAC insert was estimated to be app. 100 kb.

The sequence returned from MWG Biotech was assembled into four large contigs. These were separated by gaps that were later closed by sequencing. The annotation of BAC 1-C23 showed that 5 ORFs (designated mpaD to mpaH in FIG. 1) had similarity to polyketide biosynthesis genes. However, no putative PKS genes could be identified, as the gene cluster was located very near the end of the insert. Chances were thus that the remaining part of the MPA gene cluster could be found in another BAC. "BAC walking" subsequently indeed allowed identification of the remaining part of the MPA gene cluster.

Figures 1, 2:
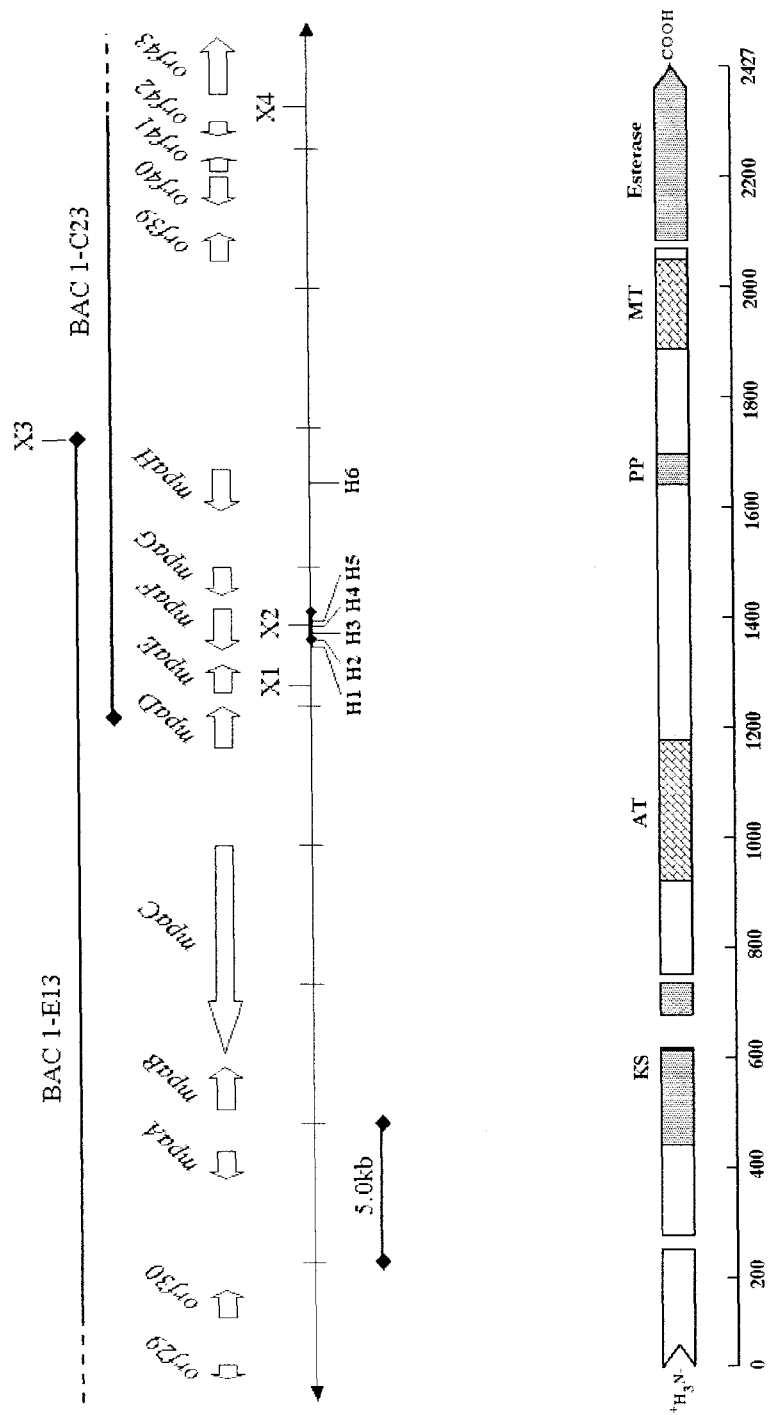
FIG. 1: The MPA biosynthesis gene cluster in *P. brevicompactum*. The gene cluster is flanked by a 4 kb and a 7 kb region with no similarity to any known sequences. These regions are therefore thought to present natural boundaries for the gene cluster. The physical map of the BACs overlapping the cluster is shown. The block arrows indicate the putative genes and their direction of transcription into mRNA based on sequence analysis and homology searches. Genes with domains that corresponded well to required enzymatic activities for MPA biosynthesis are designated mpaA-mpaH. X1-X4: XbaI restriction sites. The X3 site is located in the pECBAC1 cloning vector and is thus not part of the *P. brevicompactum* genomic DNA insert. Bold line around X2: region that hybridized with the IMPDH gene probe.
FIG. 2: Analysis of *P. brevicompactum* MpaC (polyketide synthase) (SEQ ID NO: 3) for the presence of conserved domains using the Conserved Domain Database (CDD) at the National Center for Biotechnology Information (NCBI). KS: beta-ketoacyl synthase. AT: acyltransferase. PP: phosphopantetheine attachment site. MT: Methyltransferase. Esterase: esterase domain similar to Aes of *E. coli*. Gaps indicate predicted introns.
Figure 4:
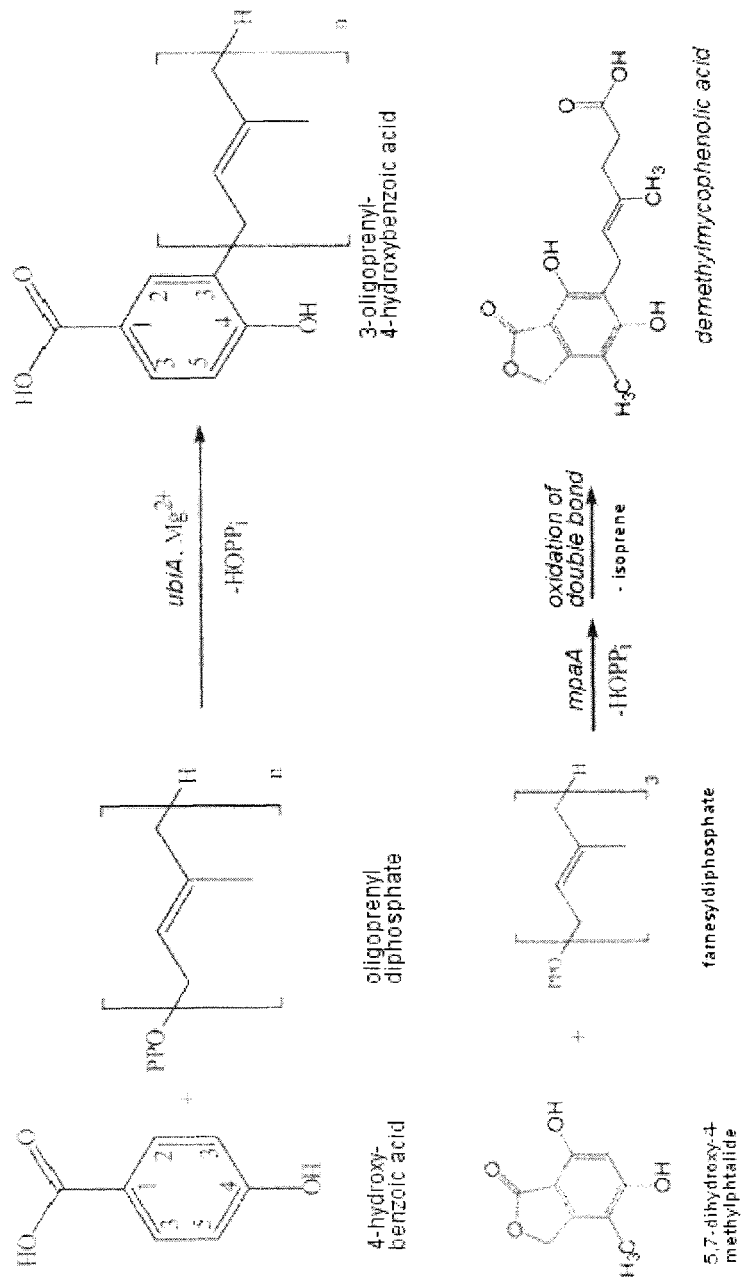
FIG. 4: Illustration of the similarities between the UbiA catalyzed prenylation reaction from *Escherichia coli* and the MpaA catalyzed reaction from *P. brevicompactum*. Hydroxyl groups function as ortho-para directing activators for the alkylation reaction. For MPA this means that the C-6 is highly activated because of the two neighbouring hydroxyl groups.

FIG. 1 shows a schematic representation of the MPA gene cluster

Example 4

Analysis of the Genes in the MPA Gene Cluster

Several of the MPA genes shown in FIG. 1 (mpaA-mpaH) have amino acid sequence homology with proteins previously shown to be involved in polyketide biosynthesis. The fragment of mpaD that was present on BAC 1-C23 was e.g. 36% identical in 192 amino acids to a cytochrome P450 involved in pisatin demethylation in *Nectria haematococca*. MpaE was 32% identical in 84 aa to AhlD, which is a zinc dependent hydrolase in *Arthrobacter* sp. MpaF was 62% identical in 524aa to IMPDH from *Candida dubliniensis*, and MpaG 30% identical in 374 aa to an Oxygen-methyl transferase B of Hypocrea virens. MpaH has weak similarity to an α/β-hydrolase fold 1 protein family.

proteins with the highest similarities to the MPA biosynthesis genes. Although, there were putative genes from *Aspergillus* spp. with higher similarities to the query sequence than the characterized homologues listed in Table 2, these were not included in the table as they do not add any information as to the function of the MPA biosynthesis genes.

As seen from Table 2, eight putative genes were identified of which only one (mpaB) encoded an enzyme with a completely unknown function. In the following examples, all the enzymes will be analyzed and discussed in detail with respect to their catalytic function in the MPA biosynthesis.

Example 5 mpaA (Encodes a Putative Prenyl Transferase; SEQ ID NO: 1)

mpaA (SEQ ID NO: 9) encodes a putative polypeptide (SEQ ID NO: 1) that contains a conserved domain that most likely belongs to the UbiA prenyltransferase family. ubiA encodes a 4-hydroxybenzoate oligoprenyltransferase in *E. coli*, and is an important key enzyme in the biosynthetic pathway to ubiquinone. It has been shown to catalyze the prenylation of 4-hydroxybenzoic acid in position 3, which is

TABLE 2

Analysis of genes in the MPA biosynthesis gene cluster

| SEQ ID NO: | Enzyme | Putative activity | Size [aa] | Predicted domains[1] and features | Closest characterized homologue | | |
|---|---|---|---|---|---|---|---|
| | | | | | Protein | Organism | Similarity |
| 1 | MpaA | Prenyl transferase | 316 | 7 transmembrane helices[2] Pfam: UbiA prenyltransferase family | (XP_746965.1) 4-hydroxybenzoate octaprenyltransferase | *Aspergillus fumigatus* | 44% in 308 aa |
| 2 | MpaB | Unknown function | 423 | TypeIII reverse signal membrane anchor[3] Pfam: None | Put. dephospho-CoA kinase (ZP_01083610) | *Synechococcus* sp. | 30% in 182 aa |
| 3 | MpaC | Polyketide synthase | 2487 | Pfam[6]: KS, AT, PP, MT, Esterase[4] | Citrinin PKS (dbj\|BAD44749.1) | *Monascus purpureus* | 32% in 2125 aa |
| 4 | MpaD | P450 monooxygenase | 535 | Possible membrane anchor[2] Pfam: Cytochrome P450 | Pisatin demethylase (P450) (gb\|AAC01762.1\|) | *Nectria haematococca* | 30% in 555 aa |
| 5 | MpaE | Zn dependent hydrolase | 261 | Pfam: Metallobeta-lactamase superfamily II | AhlD (Zn dep. hydrolase) (gb\|AAP57766.1\|) | *Arthrobacter* sp. | 32% in 84 aa |
| 6 | MpaF | Inosine monophosphate dehydrogenase | 527 | Pfam: IMPDH | IMPDH (gb\|AAW65380.1\|) | *Candida dubliniensis* | 62% in 524 aa |
| 7 | MpaG | O-methyl-transferase | 398 | Pfam: O-MT: SAM-binding motif and catalytic residues | O-methyl transferase B (gb\|ABE60721.1\|) | *Hypocrea virens* | 30% in 374 aa |
| 8 | MpaH | Hydrolase | 433 | Pfam: M-factor Weak similarity to α/β-hydrolase fold 1 | Akt2 (AK-toxin synthesis) (dbj\|BAA36589.1\|) | *Alternaria alternate* | 20% in 255 aa |

[1]By similarity to domains in the Pfam database
[2]Predicted using Phobius; accessible on the world wide web at http://phobius.cgb.ki.se
[3]Predicted using SignalP3.0; accessbile on the world wide web at www.cbs.dtu.dk.
[4]Predicted using CDD at NCBI. accessible on the world wide wed at www.ncbi.nlm.nih.gov/
[5]The GENSCAN program only predicts one intron resulting in a 548 amino acid protein. The NetAspGene 1.0 prediction server (accessible on the world wide web at www.cbs.dtu.dk) predicts two introns, which results in a 527 amino acid protein that yields an improved blastp result.
[6]KS: Ketoacylsynthase, AT: acyltransferase, PP: phosphopantheteine attachment site, MT: methyltransferase.

The closest characterized homologues in Table 2 were identified by a blastx search in public sequences with the *P. brevicompactum* DNA sequences. The column "closest characterized homologue" lists the functionally characterized similar in mechanism to the prenylation of the 5,7-dihydroxy-4-methylphtalide in the MPA biosynthesis (FIG. 7).

Figure 7:
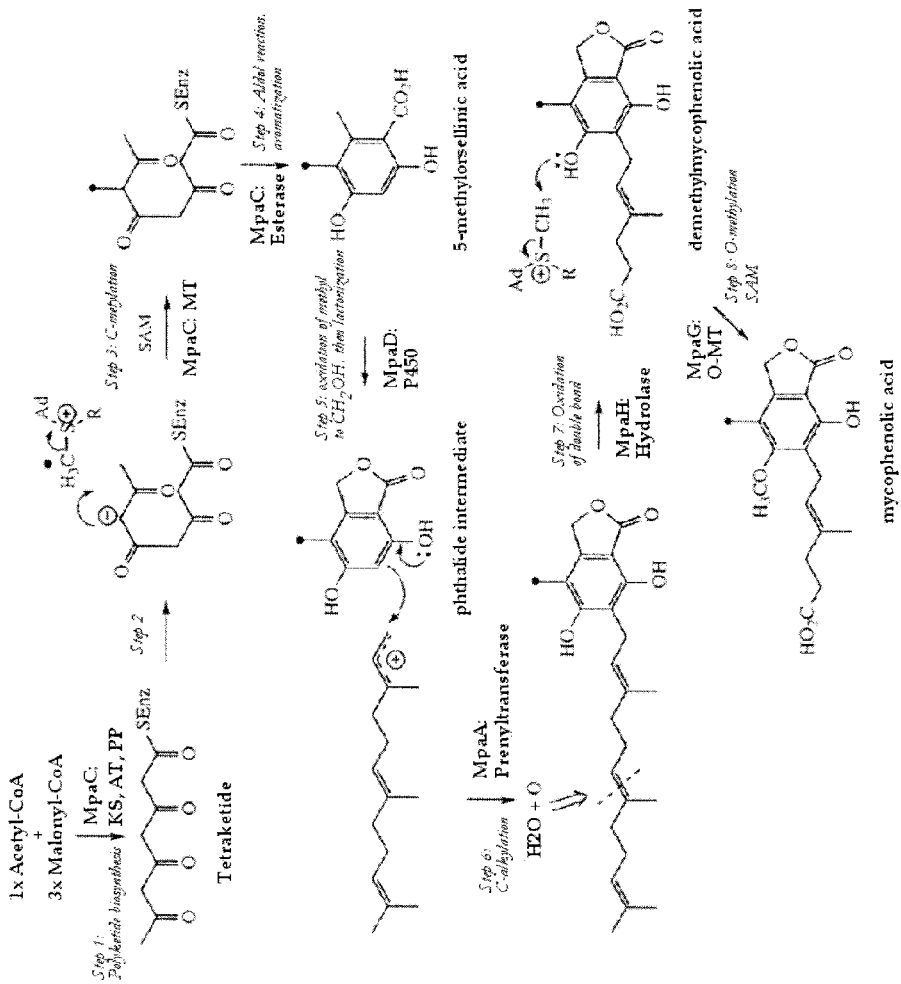
FIG. 7: Biosynthesis of MPA in *P. brevicompactum*. The putative enzymes were identified in this study and are assigned to reaction steps requiring enzymatic activities that match the predicted functions of the enzymes. Each step of the biosynthesis is numbered and used for reference in the text.

The enzymatic activity of MpaA is required at step 6 in MPA biosynthesis for the transfer of farnesyl to the dihydroxyphtalide (FIG. 7). Proteins in the UbiA-family contain seven transmembrane segments and the most conserved region is located on the external side in a loop between the second and third of these segments. Thus, if MpaA is a UbiA-family protein it should be bound to a membrane, and have its active site on the correct loop on the external side of the membrane. An analysis of MpaA using the transmembrane domain predictor, Phobius, resulted in the pattern illustrated in FIG. 5.

Figure 5:
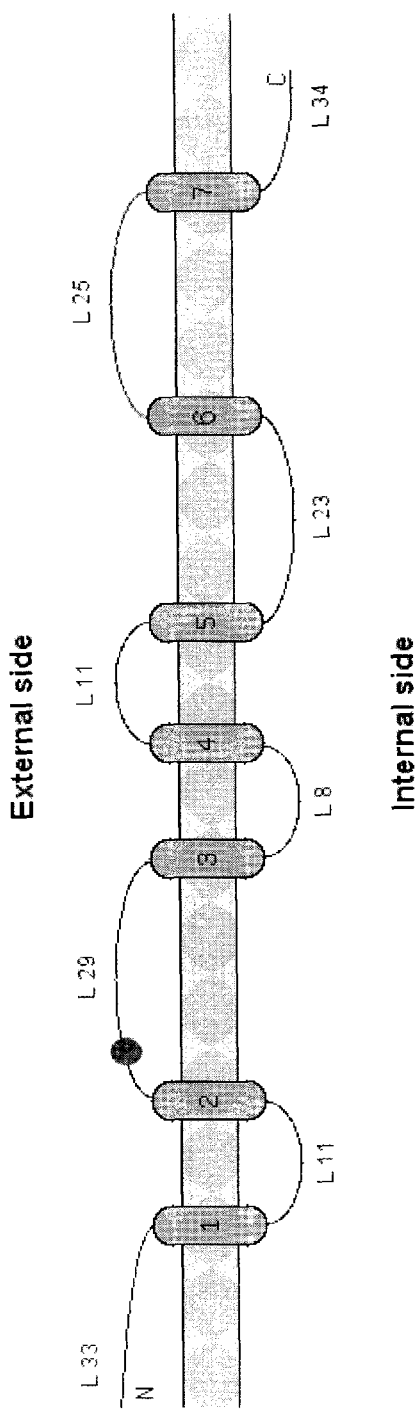
FIG. 5: Illustration of the Phobius-predicted transmembrane helices in *P. brevicompactum* MpaA (prenyl transferase) (SEQ ID NO: 1). Seven transmembrane regions were identified, and the prenyl transferase consensus pattern was found between the second and third transmembrane segments as indicated with a filled circle on loop between transmembrane region two and three. L#: number of amino acid residues in each loop.

The result in FIG. 5 strongly indicates that 7 transmembrane helices are present in MpaA as expected for an UbiA family protein. The active site was identified by searching for the active site consensus pattern characteristic for the UbiA prenyltransferase family. The UbiA phenyltransferase family has previously been characterized in Bräuer et al. (Journal of Molecular Modelling 10[5-6], 317-327. 2004).

The amino acid active site consensus pattern for an UbiaA family protein is given by:

N-x(3)-[DEH]-x(2)-[LIMFYT]-D-x(2)-[VM]-x-R-[ST]-x(2)-R-x(4)-[GYNKR]   (SEQ ID NO: 36).

Identified motif in MpaA (residue 91 to 113 of SEQ ID NO: 1):

N-dlv-D-rd-I-D-ar-V-a-R-T-km-R-plas-G.

For the active site consensus pattern counts:

Capital letter: The only amino acid allowed in a given position.

Capital letters in [ ]: Allowed amino acids in a given position.

x(#): Number of residues where all amino acids are allowed.

The identified active site was in accordance with Bräuer et al. The active site was correctly positioned between the second and third of the transmembrane segments on a loop on the external side of the membrane.

Based on sequence similarity between different prenyltransferases Bräuer et al. hypothesized that the active site is on the outside of the membrane linked to the hydrophilic diphosphate of the diphosphatefarnesyl, which has its hydrophobic acyl chain buried in the membrane.

To further substantiate the notion that MpaA is a transmembrane protein, an analysis of the myristoylation pattern was carried out as the hydrophobic acyl chains of myristoyl groups have been shown to target proteins to membranes. The myristoylation site consensus pattern is described below:

Myristoylation site consensus pattern: G-{EDRKHP-FYW}-x(2)-[STAGCN]-{P}   (SEQ ID NO: 37)

The same rules apply here as for the prenylation active site consensus pattern described above. In addition, letters in { } are not allowed in the given position. In the myristoylation site, it is the first G which is being myristoylated.

The analysis revealed three N-myristoylation sites in MpaA, two of which were positioned at residues 85-92, very close to the active site:

TABLE 4

Identified myristoylation sites in MpaA

| Residues | Sequence matching consensus sequence | SEQ ID NO |
|---|---|---|
| 85-90 | GAgnTW | 38 |
| 87-92 | GNtwND | 39 |
| 155-160 | GLaiGY | 40 |

It is probably only one of the myristoylation sites at residues 85-90 and 87-92, which is myristoylated. It may be speculated that the presence of myristoylation sites immediately prior to the prenylation active site (residues 91-113) may function as anchor points of the prenyl transferase to the membrane, thereby ensuring that the active site is localized in direct proximity of the prenyl-chain in the membrane.

The amino acid sequence spanning position 14-301 in SEQ ID NO: 1 shares 46% identity with the corresponding portion of the closest related amino acid sequence present in the database (EAW19988.1). Sequences relating to the present invention are thus at least 50% identical, preferably at least 55% identical, more preferably at least 60% identical, more preferably at least 65% identical, more preferably at least 70% identical, more preferably at least 80% identical, more preferably at least 85% identical, more preferably at least 90% identical, and most preferably at least 95%% identical with position 14-301 in SEQ ID NO: 1.

Example 6 mpaB (Encodes a Polypeptide with Unknown Function; SEQ ID NO: 2)

mpaB (SEQ ID NO: 10) encodes a putative protein of 423 amino acids with an unknown function (SEQ ID NO: 2). The most similar characterized protein is a dephospho-CoA kinase, with 30% similarity (Table 2). A putative signal targeting MpaB to membranes could be detected using SignalP3.0 software. No cleavage signal was predicted with SignalP3.0 software, and the protein is thus presumably not released from but rather anchored to the membrane. It is uncertain whether the targeting is directed towards the cytoplasmic membrane or towards intracellular membrane-contained organelles. The program predicts a hydrophilic N-terminal region, followed by a hydrophobic (H-) region that spans the membrane. The stretch of positively charged amino acid residues on the C-terminal side of the H-region indicates that this side is inside and the N terminal region of the protein is situated outside. This was confirmed by a prediction using the Phobius software.

Position 22-422 in SEQ ID NO: 2 shares 61% identity with the corresponding portion from closest related amino acid sequence available in the database (EAW07745.1). Sequences according to the preset invention thus share at least 70% identity, preferably at least 75% identity, preferably at least 80% identity, preferably at least 85% identity, more preferably at least 90% identity, and most preferably at least 95% identity with position 22-422 in SEQ ID NO: 2.

Example 7 mpaC (Encodes a Putative Polyketide Synthase (PKS); SEQ ID NO: 3)

mpaC (SEQ ID NO: 11) encodes a novel putative multifunctional type I PKS (SEQ ID NO: 3) with a GENSCAN-predicted size of 2487 aa (265 kDa). Four putative introns were identified ranging from 62 to 259 nucleotides. The enzyme shows strong similarity to other PKSs and share 32% similarity in 2125 aa to the citrinin PKS from *Monascus purpureus*, which is the characterized PKS with the highest similarity to MpaC (SEQ ID NO: 3). Two putative PKSs from *A. nidulans* and *A. terreus* share 45% similarity with MpaC in 2509 and 2375 aa, respectively. Several motifs could be detected by analyzing the amino acid sequence using the Conserved Domain Database (CDD) at the National Center for Biotechnology Information (NCBI) (FIG. 2).

All the domains necessary for a functional PKS were detected with the CDD analysis, namely the KS, AT, and PP domains (FIG. 2). As MPA is an unreduced polyketide it was consistent with the expectations that no reducing domains were identified in the CDD analysis. In addition, an MT domain was identified also in accordance with the biosynthesis which includes a methylation at the tetraketide stage. The MT domain was similar in primary structure to other MT domains identified from other PKSs like the lovastatin PKSs (LNKS, LDKS) from *A. terreus* and compactin PKSs (MlcA, MlcB) from *Penicillium solitum* (Table 3).

TABLE 3

MT domains from different fungal PKSs

| PKS | Uniprot ID | Specie | MT Residues |
|---|---|---|---|
| MlcA | dbj\|BAC20564.1 | *P. solitum* | 1395...1597 |
| MlcB | dbj\|BAC20566.1 | *P. solitum* | 1461...1590 |
| LNKS | sp\|Q9Y8A5 | *A. terreus* | 1417...1553 |
| LDKS | gb\|AAD34559.1 | *A. terreus* | 1431...1557 |
| MpaC (SEQ ID NO: 3) | Not assigned | *P. brevicompactum* | 1923...2075 |

The residues of MlcA, MlcB, LNKS, and LDKS, belonging to the MT domains were given in the Uniprot database, and for MpaC the residues were identified in the CDD analysis in FIG. 2. In order to confirm the CDD result concerning the MT domain of MpaC, the MT domains listed in 3 were aligned and the result is presented in FIG. 3.

Figure 3:
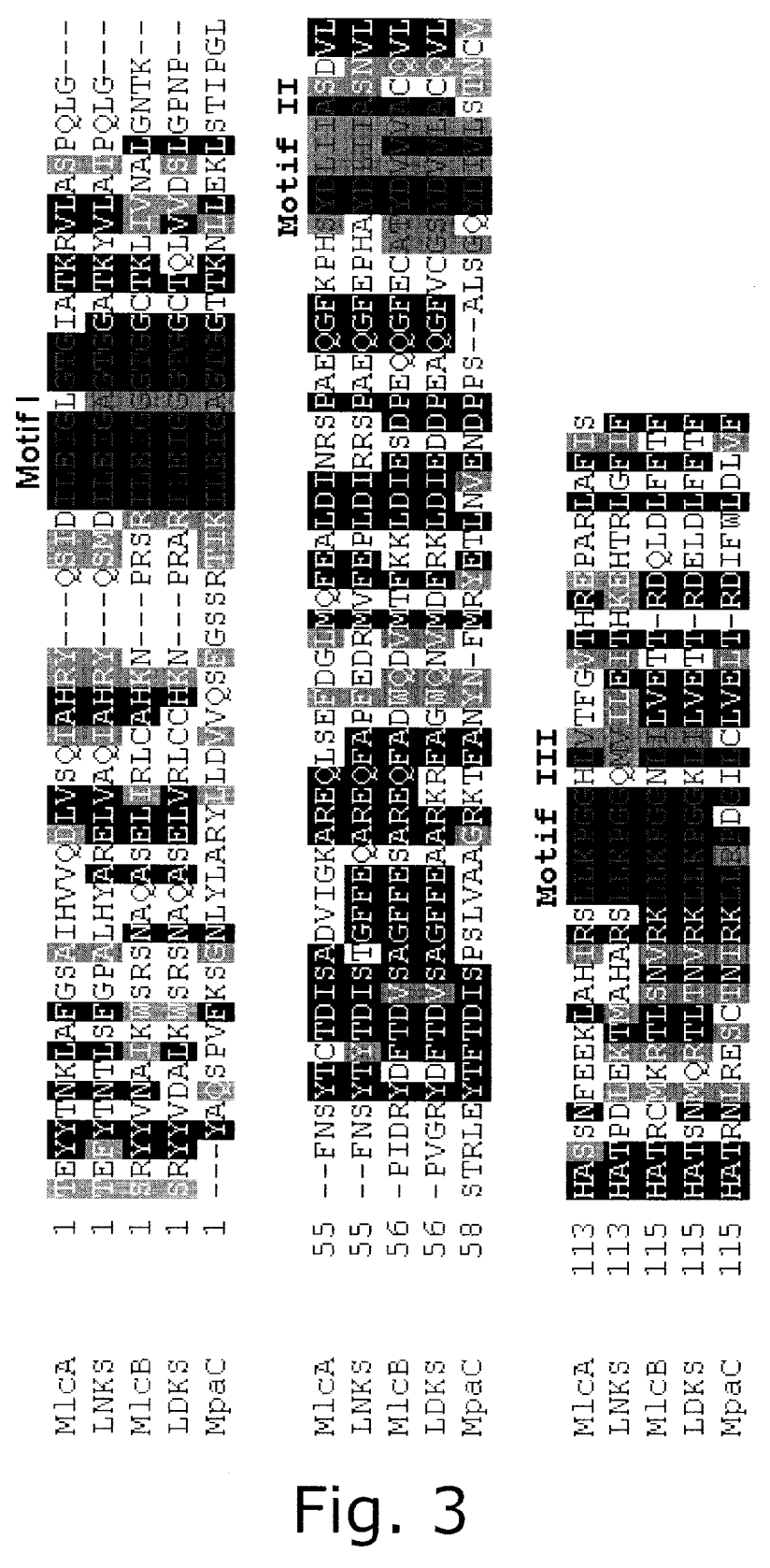

In FIG. 3, three motifs designated Motif I to III which are known to be present in most PKS MT domains, could also be identified in MpaC. The biosynthesis of MPA has been shown to involve a methylation of the tetraketide with S-adenosyl methionine as methyl donor. Hence, the presence of the MT domain is consistent with this finding, as well as the lack of reducing domains is consistent with the fact that MPA is an unreduced polyketide.

The esterase in MpaC is not homologous to any characterized thioesterases. The domain contains the α/β-hydrolase fold and is most similar to carboxylic acid esterases, which by the addition of water cleaves the carboxylic acid ester into the acid and an alcohol. The domain has similarity to the Aes protein from *E. coli*, which has been shown to hydrolyze p-nitrophenyl acetate into acetate and p-nitrophenol. Only the cleavage of the thioester between the tetraketide and the PKS requires a similar catalytic activity, and it is therefore likely that the esterase domain is involved in this step.

The amino acid sequence spanning position 10-2487 of SEQ ID NO: 3 shares 49% identity with the corresponding portion of the closest related amino acid sequence present in the database (EAA67005.1). Sequences relating to the present invention are thus at least 50% identical, preferably at least 55% identical, more preferably at least 60% identical, more preferably at least 65% identical, more preferably at least 70% identical, more preferably at least 80% identical, more preferably at least 85% identical, more preferably at least 90% identical, and most preferably at least 95%% identical with position 10-2487 in SEQ ID NO: 3.

Example 8 mpaD (Encodes a Putative p450 Monooxygenase; SEQ ID NO: 4)

mpaD (SEQ ID NO: 12) contains three introns and encodes a putative P450 monooxygenase (CDD and Pfam) of 535 amino acids (SEQ ID NO: 4). The protein contains a 10 amino acids long N-terminal H-region, which may function as a membrane anchor. SignalP3.0 predicts MpaD to be a signal protein with cleavage site after residue 25 (Signal Probability=0.61; Anchor probability=0.35; Data not shown). However, the protein is probably not secreted as the most likely putative function of the protein is oxidation of an MPA intermediate at step 5 in FIG. 7.

The amino acid sequence spanning position 24-502 of SEQ ID NO: 4 shares 54% identity with the corresponding portion of the closest related amino acid sequence present in the database (BAE65443.1). Sequences relating to the present invention are thus at least 60% identical, more preferably at least 65% identical, more preferably at least 70% identical, more preferably at least 80% identical, more preferably at least 85% identical, more preferably at least 90% identical, and most preferably at least 95%% identical with position 24-502 in SEQ ID NO: 4.

Example 9 mpaE (Encodes a Putative Hydrolase; SEQ ID NO: 5)

mpaE (SEQ ID NO: 13) encodes a putative hydrolase (COG1237: Metal dependent hydrolases of beta-lactamase superfamily II; Pfam: Metallo-beta-lactamase superfamily) of 261 amino acids (SEQ ID NO: 5). It is uncertain how many introns, if any, the gene contains as the predicted protein is based solely on the blastx result and there is no obvious startcodon based on the similarity to other proteins. Consequently, it is also impossible to predict whether or not this protein contains any signals targeting it to a specific cellular structure as these usually are localized in the C-terminal end of the protein. It is difficult to assign the putative function of MpaE as several proteins contain the lactamase domain, but none with a function that is obvious in the MPA biosynthesis. Certain thioesterases and glyoxylases contain the metallo-beta-lactamase domain, and therefore it is possible that MpaE functions as a thioesterase that cleaves the thioester linking the polyketide chain to the PKS.

The amino acid sequence spanning position 1-255 of SEQ ID NO: 5 shares 49% identity with the corresponding portion of the closest related amino acid sequence present in the database (EAT86512). Sequences relating to the present invention are thus at least 50% identical, preferably at least 55% identical, more preferably at least 60% identical, more preferably at least 65% identical, more preferably at least 70% identical, more preferably at least 80% identical, more preferably at least 85% identical, more preferably at least 90% identical, and most preferably at least 95%% identical with position 1-255 in SEQ ID NO: 5.

Example 10 mpaF (Encodes a Putative IMPDH; SEQ ID NO: 6)

mpaF (SEQ ID NO: 14) encodes a putative IMPDH protein (SEQ ID NO: 6)

The amino acid sequence spanning position 3-526 of SEQ ID NO: 6 shares 81% identity with the corresponding portion of the closest related amino acid sequence present in the database (BAE62832.1). Sequences relating to the present invention are thus at least 85% identical, more preferably at least 90% identical, and most preferably at least 95%% identical with position 10-2487 in SEQ ID NO: 3.

Example 11 mpaG (Encodes a Putative O-Methyltransferase; SEQ ID NO: 7)

mpaG (SEQ ID NO: 15) encodes a putative protein of 398 residues (43.1 kDa) and contains one intron (GENSCAN; NetAspGene 1.0) (SEQ ID NO: 7). The protein is 30% identical in 347 aa to viridin O-methyltransferase from Hypocrea vixens and 45% identical in 403 aa to a hypothetical protein from *Gibberella zeae*. The predicted domain belongs to a group of O-methyltransferases that utilize SAM as methyl donor. The structure has been determined of the related enzyme, caffeic acid-O-methyltransferase (C-O-MT), which catalyzes the methylation of the following lignin monomers in plants: caffeate, caffeoyl alcohol, caffeoyl aldehyde, 5-hydroxyferulate, 5-hydroxyconiferyl alcohol and 5-hydroxyconiferyl aldehyde. By comparing the deduced MpaG amino acid sequence to O-MT proteins with similar functions, it was possible to estimate if the required domains are present in MpaG. The selected sequences for this purpose are listed in Table 5.

TABLE 5

O-MT proteins used for alignment with MpaG

| Protein | Uniprot ID | Species |
|---|---|---|
| MpaG (SEQ ID NO: 7) | Not assigned | *P. brevicompactum* |
| O-MT B | gb|ABE60721.1| | *Hypocrea wrens* |
| O-MT B | gb|AAS66016.1| | *A. parasiticus* |
| Hyp. O-MT[1] | gb|EAA69894.1| | *Gibberella zeae* |
| Caffeoyl-O-MT (C-O-MT) | gb|AAB46623.1| | *Medicago sativa* |

[1]Hyp. O-MT: hypothetical O-MT - was identified in the annotation of the MPA gene cluster, where it was the blastx hit with the highest score to mpaG.

Figure 6:
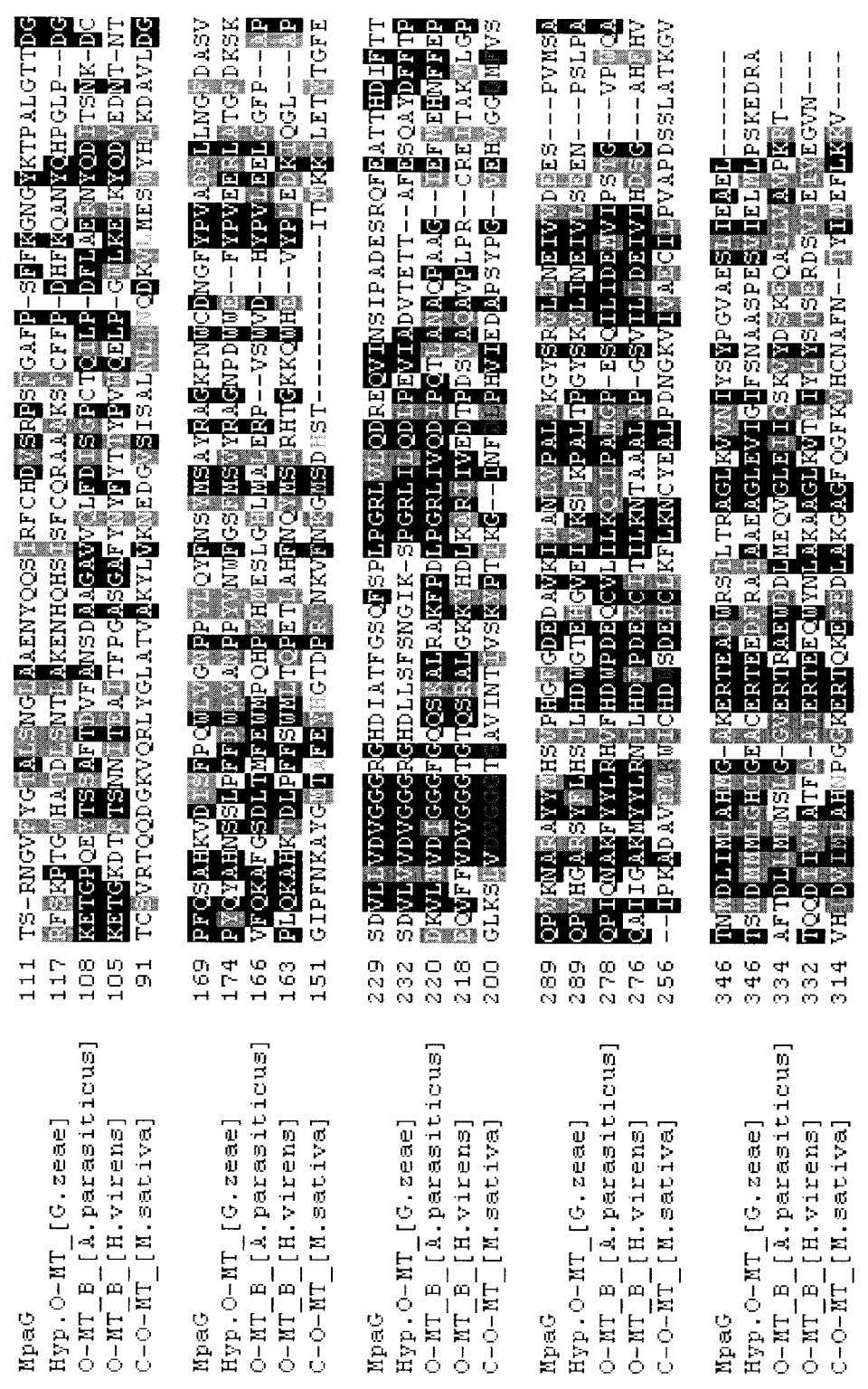

In the alignment of the sequences from Table 5 the first 90 residues were omitted as seen in FIG. 6.

The O-MT B protein of H. vixens seems to be involved in antibiotic production and the O-MT B from *A. parasiticus* is involved in aflatoxin production.

The proteins have locally conserved domains such as the SAM binding site and certain catalytic residues. However, apart from those conserved domains, the proteins are very diverse which is consistent with the fact that the substrates of the enzymes structurally are very different.

The amino acid sequence spanning position 5-397 of SEQ ID NO: 7 shares 45% identity with the corresponding portion of the closest related amino acid sequence present in the database (XP_382791.1). Sequences relating to the present invention are thus at least 50% identical, preferably at least 55% identical, more preferably at least 60% identical, more preferably at least 65% identical, more preferably at least 70% identical, more preferably at least 80% identical, more preferably at least 85% identical, more preferably at least 90% identitcal, and most preferably at least 95% identical with position 5-397 in SEQ ID NO: 7.

Example 12 mpaH (Encodes a Putative Hydrolase; SEQ ID NO: 8)

mpaH (SEQ ID NO: 16) encodes a putative protein of 433 amino acids and minimum two introns as predicted with NetAspGene 1.0 and blastx similarity searches (SEQ ID NO: 8). The protein is 20% identical in 255aa to Akt2 and has a weak similarity to an M-factor domain (Pfam analysis: E-value=0.12) and a hydrolase 1 domain (Pfam analysis: E-value=0.9). MpaH is 35% similar to a hypothetical protein from *A. fumigatus* in 448 amino acids, which is a putative toxin biosynthesis protein due to its similarity to Akt2. Akt2 has an unknown function in the biosynthesis of the AK-toxin 2, produced by a Japanese pear specific variant of *Alternaria alternata*. These proteins contain a hydrolase domain with unkown substrate specificity. Thus, the most likely catalytic function in the MPA synthesis is hydrolysis of the farnesyl side chain at step 7, yielding demethylmycophenolic acid.

The amino acid sequence spanning position 1-420 of SEQ ID NO: 8 shares 69% identity with the corresponding portion of the closest related amino acid sequence present in the database (CAK48380.1). Sequences relating to the present invention are thus at least 75% identical, more preferably at least 80% identical, more preferably at least 85% identical, more preferably at least 90% identitcal, and most preferably at least 95%% identical with position 10-2487 in SEQ ID NO: 8.

Example 13

MPA Biosynthesis in *P. Brevicompactum* in Relation to the MPA Gene Cluster

In the MPA biosynthesis a tetraketide backbone aromatic ring and a farnesylgroup are fused, but only the genes necessary for the polyketide structure and postmodifications are found within the identified gene cluster. The farnesyl-CoA is produced by the normal mevalonate pathway in the fungus. The MPA biosynthesis with enzymes identified in this study assigned to each reaction step is presented in FIG. 7.

The tetraketide product of step 1 in FIG. 7 is catalyzed by MpaC, that belongs to a group classified as "fungal non-reducing methylating PKS". The methylation of C-4 at step 3 in FIG. 7 occurs after the tetraketide has been synthesized, as the two neighbouring carbonyl groups at C-3 and C-5 activate the central methylene, and thereby yielding it more reactive for methylation. MpaC contains only one PP domain and may or may not contain a cyclase domain. The predicted esterase domain at the N-terminal end of the protein may catalyze the cyclization, aromatization and release of the polyketide from the PKS. Thioesterases, which belong to the same family of proteins, have previously been reported to be involved in chain-length determination, cyclization and lactonization (Fujii et al., 2001a). However, the esterase in MpaC is not homologous to any characterized thioesterases but may well belong to a new group of fungal cyclization domains. Thus, it is listed at step 4 in FIG. 7 that the esterase domain of MpaC catalyzes the cyclization, aromatization and cleavage of the thioester linkage between the polyketide and the PKS. As one may notice from FIG. 7, 5-methylorsellinic acid, which is the first stable intermediate from the MPA biosynthesis, does not contain the lactone group. Hence, the PKS does not catalyze the lactonization but only cyclization, the following enolization and release of the polyketide from the PKS at step 4.

For lactonization to occur at step 5, the C-3-methyl group must be oxidized to the alcohol, which is a reaction often catalyzed by P450 monooxygenases. In the gene cluster, only MpaD has similarity to a P450 monooxygenase. It has been reported that the 3,5-dihydroxyphtalic acid was produced by *P. brevicompactum*, which is probably derived from orsellinic acid. Orsellinic acid methyl group oxidized to carboxylic acid yields 3,5-dihydroxyphtalic acid. As the oxidations of the C-3 methyl group of MPA and orsellinic acid mechanistically are very similar, MpaD is likely to catalyze both reactions. MpaD has a possible membrane anchor domain linking the reaction to an intracellular organelle. This corresponds well to the fact that the prenyltransferase, MpaA, which catalyzes the subsequent reaction (step 6) is membrane bound with seven transmembrane hydrophobic regions. The P450 converts the 5-methylorsellinic acid to the phthalide in close proximity to the prenyltransferase, which then adds the farnesyl side chain to the aromatic ring. It is hypothesized, that a myristoylation site in close proximity to the active site of MpaA when myristoylated functions as an anchor point of the protein to the membrane. In this way, the active site is maintained close to the farnesyl pyrophosphate, which is buried in the membrane.

The step following prenylation in the MPA biosynthesis is an oxidation of either the terminal or central double bond of the farnesyl chain (step 7). The mechanism has been reported to include an epoxidation of the double bond, followed by hydrolysis. The hydrolysis may be catalyzed by MpaE or MpaH, which both have similarities to hydrolases. MpaE, however, has similarity to a Metallo-β-lactamase, AhlD, which is involved in the degradation of the lactone of N-acyl homoserine lactone. Thus, MpaE is not thought to be involved in the hydrolysis of the farnesyl-chain. MpaH, on the other hand, has certain similarity to a Pfam category, α/β-hydrolase fold 1, which includes the enzyme class of epoxide hydrolases. Hence, MpaH is more likely to hydrolyze the epoxide intermediate than MpaE. As the prenylation of the phthalide occurs in the microsomal membranes, one may speculate that the hydrolysis of the farnesyl-chain also takes place in a microsomal membrane. The enzyme MpaB (Table 2) contains a putative membrane anchor and could thus also be involved in the farnesyl double bond oxidation. However, no putative hydrolytic or oxidative domains were detected by conserved domain analyses, which is the reason why this function is not assigned to MpaB.

The final step in the MPA biosynthesis is methylation of the 5-hydroxyl group, which is catalyzed by MpaG, the only O-methyltransferase in the MPA biosynthesis gene cluster (Table 2).

When describing gene clusters responsible for the production of secondary metabolites, it is always worthwhile investigating the factors that potentially initiate the production, which for example is the case for MlcR in the compactin gene cluster. However, no such transcription factors could be identified within the MPA biosynthesis gene cluster, and so the regulation must be further elucidated by correlating the transcription profiles at different media and conditions with the MPA production. However, such studies of the MPA production have already demonstrated that MPA is produced during growth and not only during the stationary phase where most other secondary metabolites are produced. Thus, the question is if there are any conditions where the strain does not produce MPA and if any regulation of the MPA biosynthesis genes in *P. brevicompactum* is existing.

In the MPA gene cluster it is only MpaB (SEQ ID NO: 2), MpaE (SEQ ID NO: 5) and MpaH (SEQ ID NO: 8) which cannot be assigned a specific role in the biosynthesis or resistance mechanism. However, most likely these enzymes are involved in the oxidation of the farnesyl chain or in an unresolved part of the resistance mechanism.

Example 14

The *P. brevicompactum* MPA Resistance Mechanism

*P. brevicompactum* produces MPA in order to achieve a competitive advantage over other organisms, which are inhibited by MPA. Hence, obviously *P. brevicompactum* needs to overcome the inhibitory effect from MPA. MPA inhibits the IMPDH-catalyzed conversion of IMP to XMP. In this reaction, IMP binding precedes that of nicotinamide adenine dinucleotide (NAD), and reduced nicotinamide adenine dinucleotide (NADH) is released prior to XMP. MPA binds to IMPDH after NADH is released but before XMP is produced and thus functions as an uncompetitive inhibitor.

The presence of this mechanism means that according to a preferred embodiment of the present invention, an additional IMPDH gene is present in the host cell, unless the host strain genome harbours several IMPDH copies and/or encode IMPDH copies that are fully or partly MPA-resistant. IMPDH "redundancy" thus allows the host cell to grow despite the presence of the MPA which is produced in the host cell culture.

Example 15

Heterologous MPA Production

One or more expression vectors encoding one or more of the MPA synthesis enzymes from *P. brevicompactum* is/are inserted into a host cell. If the host cell is fully or partly MPA resistant, then it may be optional to insert IMPDH encoding sequences in the host cell. The host cell is preferably a fungal organism which is relatively easy to cultivate—such as e.g. yeast. The host cell could in principle be any cell, including a bacterial cell, a mammalian cell or a plant cell. However, in order to ensure correct post translational modification which may be vital for enzyme function, the invention works most efficiently in eukaryotic, preferably fungal organisms. For practical reasons, yeast is a preferred host cell since it is generally easy to cultivate on an industrial scale.

The host cell is inoculated into a suitable growth medium that may be liquid, semi-liquid or solid and incubated under suitable conditions such that MPA production takes place. After an appropriate incubation period, the MPA containing medium is harvested from the cell culture.

Example 16

Recovering of MPA

MPA is usually recovered from growth media by organic extraction followed by distillation and crystallization techniques.

Example 17

Improved MPA Yield in *P. Brevicompactum*

The present invention can also be used to improve MPA yield in *Penicillium* spp. producing MPA naturally. In one embodiment, one or more regulatory sequences could be altered to obtain a stronger expression of one or more MPA enzymes. In another embodiment MPA production is increased by addition of additional MPA gene copies. In a third embodiment, it is envisaged that one or more of the natural MPA gene cluster promoters are stimulated to increase MPA biosynthesis and/or to obtain a constitutive MPA synthesis. In a fourth embodiment, the present invention can be carried using a fungal strain that contains increased amounts of the precursor(-s) "farnesyl diphosphate" and/or acetyl CoA. The invention may also be carried out by a mixture of these embodiments.

The advantages of using *P. brevicompactum* (or another fungus that naturally produces MPA) as a host cell for improved MPA yield are obvious:
  i) It is hypothesized that the enzymes are subject to correct post translational modification thus ensuring synthesis of functional enzymes;
  ii) It is more than likely that organisms with the capability of producing MPA harbour several unidentified mechanisms aiding the fungus in the MPA resistance, thus obtaining relatively stable and reliable growth despite high MPA concentrations;
  iii) Improved yield of MPA can be obtained with only minor alterations of existing MPA production facilities and production procedures.

The fungus may be used in the form of a spore suspension or in mycelial form. The solid substrate matrix is e.g. selected from wheat bran, rice bran, ragi flour, soya flour, cotton seed flour, wheat flour, rice flour, rice husk, or any mixture thereof. Preferred incubation conditions are moist and aerobic conditions ranging from 20-35° C. (preferably 25-30° C.) at 1-30 days (preferably 1-2 weeks). Any methods for culturing *P. brevicompactum* can be employed. Well known methods are described e.g. in U.S. Pat. No. 4,452,891.

MPA can subsequently be recovered by conventional procedures.

In the following examples (18-21) construction of mpaC deletion mutants are described.

Example 18

Construction of Gene Targeting Substrates

Figure 8:
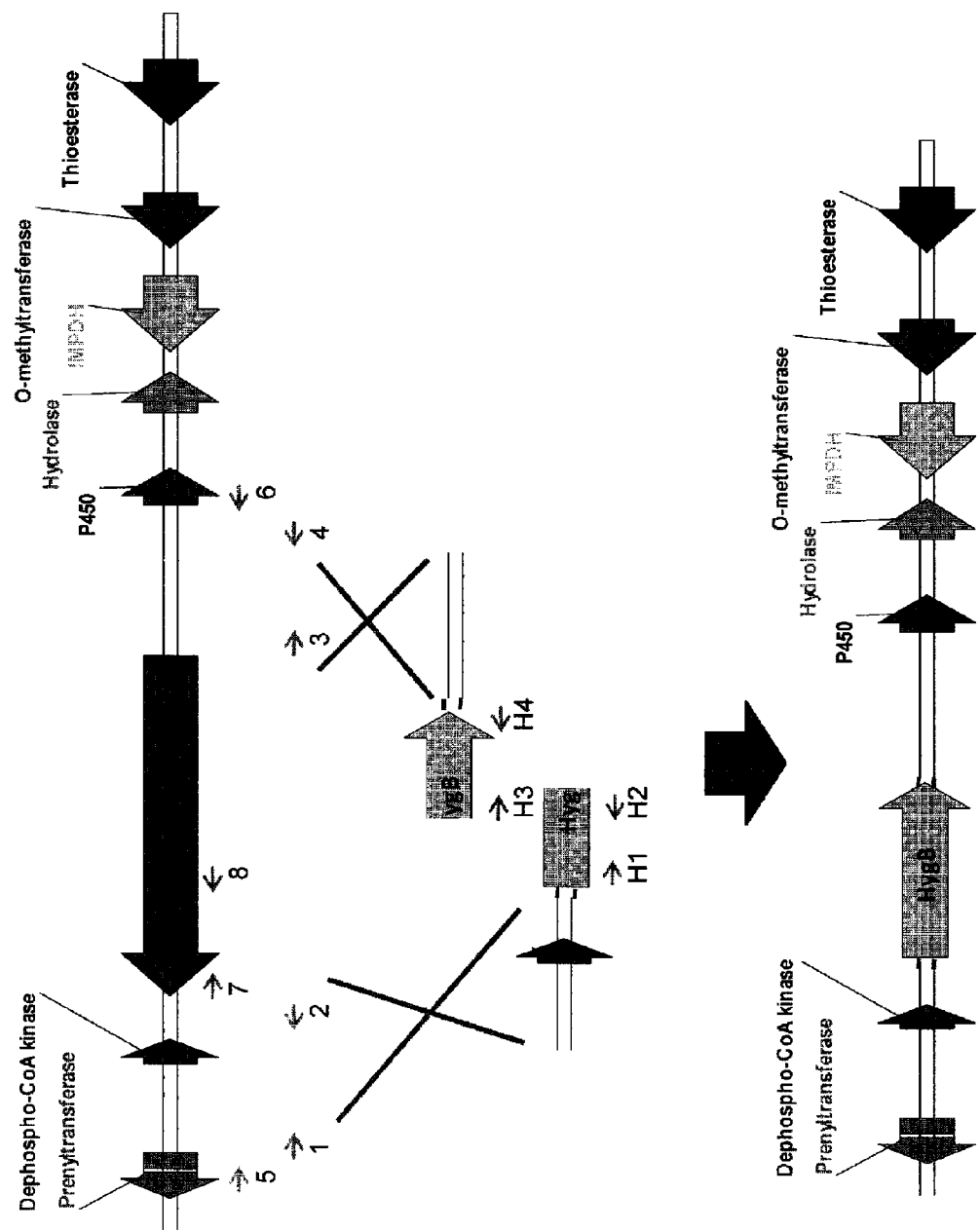
FIG. 8: Schematic representation of the bipartite gene targeting method. Grey arrows (→) represent primers used to construct gene targeting substrates.

One way to determine whether mpaC, a putative PKS, is responsible for the biosynthesis of MPA, is to delete the gene from the genome and record the consequence on the MPA productivity. Hence, we constructed several mpaC deletion mutants which all showed much reduced MPA productivities. To construct the mpaC deletion strain, the bipartite gene targeting method was used and the hygromycin resistance gene (hph) was used as a selectable marker as illustrated in FIG. 8. Each part of the fragment of bipartite substrates consists of a targeting fragment and a marker fragment. In order to enhance the homologous recombination efficiency, approximately 2.7 kb of both upstream and downstream flanking regions of mpaC were used. The upstream (2.65 kb) and downstream (2.67 kb) sequences flanking mpaC were amplified from genomic DNA of *P. brevicompactum* IBT23078 using primer pairs KO-MpaC-UF (SEQ ID NO: 21)/KO-MpaC-URa (SEQ ID NO: 22) and KO-MpaC-DFa (SEQ ID NO: 23)/KO-MpaC-DR (SEQ ID NO: 24), respectively. The two fragments containing hygromycinB resistance cassette (HygB) were amplified from pAN7-1, a vector carrying the HygB cassette. The upstream 2/3 HygB cassette (1.72 kb) was amplified using primers Upst-HygF-b (SEQ ID NO: 25) and Upst-HygR-N (SEQ ID NO: 26), whereas the downstream 2/3 HygB cassette (1.64 kb) was amplified using primers Dwst-HygF-N (SEQ ID NO: 27) and Dwst-HygR-A (SEQ ID NO: 28). A schematic overview of the gene targeting method is illustrated in FIG. 8.

To obtain the first fragment of bipartite substrate, the upstream mpaC and upstream 2/3 HygB fragments were fused together by PCR using primers KO-MpaC-UF (SEQ ID NO: 21) and Upst-HygR-N (SEQ ID NO: 26). Similarly, the second fragment of bipartite substrate was generated by fusing the downstream 2/3 HygB and downstream mpaC fragments together using primers Dwst-HygF-N (SEQ ID NO: 27) and KO-MpaC-DR (SEQ ID NO: 24).

Primers used to generate bipartite PCR fragments and to investigate the targeting pattern are listed in table 6.

TABLE 6

List of primers used in this work.

| Primer name | Sequence |
|---|---|
| Upstream mpaC | |
| 1. KO-mpaC-UF | GAGGTGACCGCTACGTGTGT |
| 2. KO-mpaC-URa | GATCCCCGGGAATTGCCATGCGTGCTGCGATACT CATTGC |

TABLE 6-continued

List of primers used in this work.

| Primer name | Sequence |
|---|---|
| Downstream mpaC | |
| 3. KO-mpaC-DFa | GGACTGAGTAGCCTGACATCGGTCGTAAGCCTTG GCTGTG |
| 4. KO-mpaC-DR | CCTACGCGGTTTCCTGAGTT |
| Hygromycin cassette | |
| H1. Upst-HygF-b | catggcaattcccggggatcGCTGATTCTGGAGT GACCCAGAG |
| H2. Upst-HygR-N | CTGCTGCTCCATACAAGCCAACC |
| H3. Dwst-HygF-N | GACATTGGGGAATTCAGCGAGAG |
| H4. Dwst-HygR-A | gatgtcaggctactcagtccCGTTGTAAAACGAC GGCCAGTGC |
| Primers for checking targeting status | |
| 5. KO-mpaC-F1 | CAGACGGCAGACAACCGAGA |
| 6. KO-mpaC-Re3 | TGGGCTCGTATTTGACTCCG |
| 7. KO-2mpaC-UF | GGACACACGTAGGCAATGAGT |
| 8. KO-2mpaC-URa | GGTGGCACCACAAGCTGTAT |

Example 19

Transformation of *P. brevicompactum* IBT23078

Genetic transformation of *P. brevicompactum* IBT23078 was carried out according to a slightly modified version of the procedure described by Nielsen M L, Albertsen, L, and Mortensen, U H. 2005 in "Genetic stability of direct and inverted repeats in *Aspergillus nidulans*", *Journal of Biotechnology* 118:S13. 21-hour-old fungal mycelium was used for protoplast preparation. All transformation experiments were performed with $2\times10^5$ protoplasts in 200 µl transformation buffer. 1-2 µg of each purified fusion PCR fragments were used for transformation. Selection of transformants was done on selective minimal medium (MM) containing 1M sorbitol, 2% glucose and 300 µg/ml hygromycin. For the positive control experiment, *P. brevicompactum* IBT23078 was transformed with pAN7-1 plasmid carrying the HygB cassette. Several transformants were observed after 4-5 days of incubation at 25° C. Transformants were purified by streaking out spores to obtain single colonies on selective minimal medium containing 150 µg/ml hygromycin and incubated at 25° C. for 4-5 days. The resulting transformants were further purified twice on fresh selective medium. 20 purified transformants were selected for further investigation.

Example 20

Analysis of Transformants

Each purified transformant was three points inoculated on Yeast Extract Sucrose (YES) agar (20 g/L yeast extract, 150 g/L sucrose, 0.5 g/L MgSO$_4$.7H$_2$O, 0.01 g/L ZnSO$_4$.7H$_2$O, 0.005 g/L CuSO$_4$.5H$_2$O, 20 g/L agar) and incubated at 25° C. for 5 days. Total genomic DNA from each clone was isolated and the integration pattern of the HygB cassette was investigated by PCR and sequencing. For isolation of genomic DNA, 40-50 mg mycelia were taken from YES agar and transferred to 2 ml Eppendorf tubes containing steel balls (2×Ø 2 mm, 1×Ø5 mm). The mycelium was frozen in liquid nitrogen and homogenized in a Mixer Mill for 10 min at 4° C.

The resulting powder was used for genomic DNA extraction using FastDNA® Spin Kit for Soil (Qbiogene, Inc.).

Figure 9:
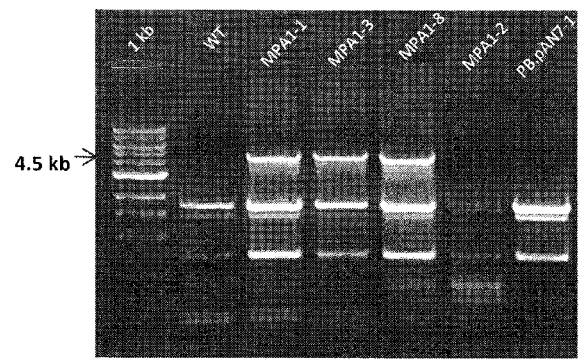
FIG. 9: The following abbreviations are used in the figure: WT, the wild-type strain IBT23078; PB-pAN7-1, IBT23078 transformed with pAN7-1 plasmid; MPA1-1, MPA1-2, MPA1-3 and MPA1-8, IBT 23078 transformed with bipartite substrates.
Figure 9:
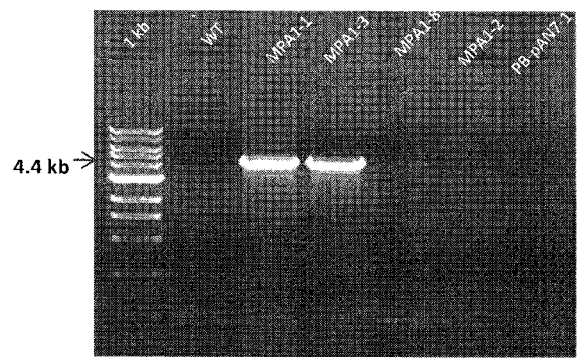
Figure 9:
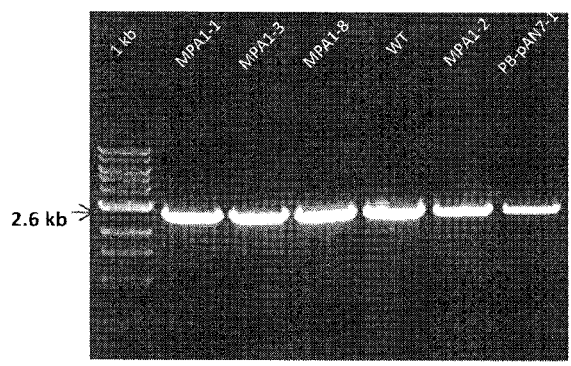

In order to investigate the integration events, two PCR experiments were performed. Both PCR experiments were performed by using primer pairs in which one of the primers is located outside the homologous region and the other is located in the HygR cassette. FIGS. 9A and 9B showed the results from amplification of the upstream and downstream region of mpaC from the wild-type and some transformants. Out of 20 transformants, the following 9 transformants were found to be the correct mpaC deletion strains: MPA1-1, MPA1-3, MPA1-8, MPA2-3, MPA2-4, MPA2-5, MPA2-6, MPA2-7 and MPA2-9. The remaining 11 transformants must have appeared due to non-homologous integration. As expected, the wild-type and transformants derived from non-homologous recombination gave no PCR product when checked for integration at the mpaC locus.

An additional PCR reaction was performed to investigate the presence of mpaC in the transformants (FIG. 9C). Surprisingly, a 2.6 kb PCR product corresponding to 1/3 of mpaC was detected in all strains including the mpaC deletion strains. Therefore, PCR fragments analogous to those illustrated in FIGS. 9A and 9B of 4 mpaC deletion strains (MPA1-1, MPA1-3, MPA2-5 (not in FIG. 9A/B), MPA2-9 (not in FIG. 9A/B)) were further characterized by sequencing using primers located at both ends of each PCR fragments. Sequencing results confirmed that those strains were the correct mpaC deletion strains.

Example 21

Metabolites Analysis of mpaC Deletion Strains

Metabolites were extracted from both the parental strain and the mpaC deletion strains grown on YES agar at 25° C. for 5 days and investigated by HPLC. Six plugs (6 mm in diameter) were taken from each culture, transferred to a 2-ml vial and extracted with 1 ml ethyl acetate containing 0.5% (v/v) formic acid on an ultrasonication bath for 60 minutes. The ethyl acetate extract was transferred to a new vial and evaporated to dryness in a rotary vacuum concentrator (RVC; Christ Frees Drier, USA). The dried extracts were re-dissolved with 400 µl methanol ultrasonically (10 minutes) and filtered through 0.45-µm Minisart RC4 filter (Sartorius, Germany) into a clean vial before HPLC analysis.

The HPLC profile of the wild-type and some transformants are shown in FIG. 10. The relative amount of mycophenolic acid produced from all strains is shown in FIG. 10. Of the 20 strains tested, 35 to 64% reduction in MPA productivity was observed by exactly those 9 strains that were AmpaC. Exactly those 9 mutants that the PCR analyses verified as AmpaC, are identified in FIG. 11 with 35 to 64% lower MPA productivity as compared to the wild type. This confirms, that mpaC is involved in the MPA production in P. brevicompactum.

Based on both PCR and HPLC results, it is concluded that 9 strains (MPA1-1, MPA1-3, MPA1-8, MPA2-3, MPA2-4, MPA2-5, MPA2-6, MPA2-7 and MPA2-9) are the correct mpaC deletion strains and that the mpaC gene is involved in mycophenolic acid production. This result is clear despite the fact that the production of mycophenolic acid in those strains was not completely abolished, which corresponds with the PCR results shown in FIG. 9C indicating that mpaC is somehow still present in all of these strains. There may be several explanations for this phenomenon; P. brevicompactum might have more than one copy of the chromosome as known from Saccharomyces cerevisiae or heterokaryons between the deletion and non-deletion strains were formed during the transformation experiments. More likely, however, P. brevicompactum forms multikaryous protoplasts, i.e. protoplasts containing more than one nuclei of which only part of them are transformed during transformation. This explains well the obtained PCR fragments as well as the substantial reduction in MPA productivity.

In conclusion the performed experiments show that mpaC is a key gene involved in the production of MPA by P. brevicompactum.

The invention claimed is:

1. An expression vector comprising a polynucleotide that encodes a polypeptide that has an amino acid sequence that is at least 90% identical to the sequence set forth in SEQ ID NO: 3, wherein said polypeptide is a polyketide synthase.

2. An expression vector comprising a polynucleotide that encodes a polypeptide that has an amino acid sequence that is at least 90% identical to the sequence set forth in SEQ ID NO: 6, wherein said polypeptide is an inosine monophosphate dehydrogenase.

3. An expression vector comprising a polynucleotide that is at least 90% identical to the sequence set forth in SEQ ID NO:11, wherein said polynucleotide encodes a polyketide synthase.

4. The expression vector of claim 1, wherein said polynucleotide encodes a polypeptide that has the amino acid sequence set forth in SEQ ID NO: 3, wherein said polypeptide is a polyketide synthase.

5. The expression vector of claim 2, wherein said polynucleotide encodes a polypeptide that has the amino acid sequence set forth in SEQ ID NO: 6, wherein said polypeptide is a inosine monophosphate dehydrogenase.

6. The expression vector of claim 3, wherein said polynucleotide comprises the sequence set forth in SEQ ID NO: 11, wherein said polypeptide is a polyketide synthase.

7. A host cell comprising the expression vector of claim 1.

8. A host cell comprising the expression vector of claim 2.

9. The host cell of claim 7, wherein the cell is a fungus.

10. The host cell of claim 8, wherein the cell is a fungus.

11. The host cell of claim 7, wherein said cell is a *Penicillium*.

12. The host cell of claim 8, wherein said cell is a *Penicillium*.

13. The host cell of claim 7, wherein said cell is *Penicillium brevicompaetum*.

14. The host cell of claim 8, wherein said cell is *Penicillium brevicompaetum*.

15. A method of cultivating the host cell of claim 7 comprising:
providing the host cell; and
growing said host cell in a growth medium under appropriate conditions.

16. A method of cultivating the host cell of claim 8 comprising:
providing the host cell; and
growing said host cell in a growth medium under appropriate conditions.

17. The method of claim 15, further comprising recovering mycophenolic acid (MPA) from said growth medium.

18. The method of claim 15, wherein said host cell is *Penicillium brevicompactum*.

19. The method of claim 15, further comprising recovering mycophenolic acid (MPA) from said growth medium.

20. The method of claim 15, wherein said host cell is *Penicillium brevicompactum*.

21. The expression construct of claim 1, further comprising a polynucleotide encoding a polypeptide of the sequence set forth in SEQ ID NO: 1, SEQ ID NO: 2, SEQ ID NO: 4, SEQ ID NO: 5, SEQ ID NO: 6, SEQ ID NO: 7 or SEQ ID NO: 8.

22. The expression construct of claim 2, further comprising a polynucleotide encoding a polypeptide of the sequence set forth in SEQ ID NO: 1, SEQ ID NO: 2, SEQ ID NO: 3, SEQ ID NO: 4, SEQ ID NO: 5, SEQ ID NO: 7 or SEQ ID NO: 8.

* * * * *

UNITED STATES PATENT AND TRADEMARK OFFICE
CERTIFICATE OF CORRECTION

PATENT NO. : 8,420,378 B2
APPLICATION NO. : 12/663773
DATED : April 16, 2013
INVENTOR(S) : Jens Bredal Nielsen et al.

It is certified that error appears in the above-identified patent and that said Letters Patent is hereby corrected as shown below:

In the Specification

In Column 1, Line 40, Change "Pencicillum" to --Penicillium--.

In Column 7, Line 52, Change "therpeutical" to --therapeutical--.

In Column 8, Line 24, Change "Filibasidium," to --Filobasidium,--.

In Column 11, Line 8, Change "cluster" to --cluster.--.

In Column 11-12 (Table 2), Line 36, Change "wed" to --web--.

In Column 11-12 (Table 2), Line 39, Change "phosphopantheteine" to --phosphopantetheine--.

In Column 12, Line 65, Change "methylphtalide" to --methylphthalide--.

In Column 12-13, Line 67 (Col. 12), Line 1 (Col. 13), Change "methylphtalide" to --methylphthalide--.

In Column 16, Line 32, Change "glyoxylases" to --glyoxalase--.

In Column 17, Line 22, Change "wrens" to --virens--.

In Column 17, Line 30, Change "vixens" to --virens--.

In Column 17, Line 47, Change "identitcal," to --identical,--.

In Column 17, Line 65, Change "unkown" to --unknown--.

In Column 18, Line 7, Change "identitcal," to --identical,--.

In Column 18, Line 50, Change "dihydroxyphtalic," to --dihydroxyphthalic--.

In Column 18, Line 53, Change "dihydroxyphtalic," to --dihydroxyphthalic--.

In the Claims

In Column 77, Line 6, In Claim 13, Change "brevicompaetum." to --brevicompactum.--.

In Column 77, Line 8, In Claim 13, Change "brevicompaetum." to --brevicompactum.--.

Signed and Sealed this
Eighth Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,420,378 B2
APPLICATION NO. : 12/663773
DATED : April 16, 2013
INVENTOR(S) : Jens Bredal Nielsen et al.

It is certified that error appears in the above-identified patent and that said Letters Patent is hereby corrected as shown below:

In the Specification

In Column 1, Line 40, Change "Pencicillum" to --Penicillium--.

In Column 7, Line 52, Change "therpeutical" to --therapeutical--.

In Column 8, Line 24, Change "Filibasidium," to --Filobasidium,--.

In Column 11, Line 8, Change "cluster" to --cluster.--.

In Column 11-12 (Table 2), Line 36, Change "wed" to --web--.

In Column 11-12 (Table 2), Line 39, Change "phosphopantheteine" to --phosphopantetheine--.

In Column 12, Line 65, Change "methylphtalide" to --methylphthalide--.

In Column 12-13, Line 67 (Col. 12), Line 1 (Col. 13), Change "methylphtalide" to --methylphthalide--.

In Column 16, Line 32, Change "glyoxylases" to --glyoxalase--.

In Column 17, Line 22, Change "wrens" to --virens--.

In Column 17, Line 30, Change "vixens" to --virens--.

In Column 17, Line 47, Change "identitcal," to --identical,--.

In Column 17, Line 65, Change "unkown" to --unknown--.

In Column 18, Line 7, Change "identitcal," to --identical,--.

In Column 18, Line 50, Change "dihydroxyphtalic," to --dihydroxyphthalic--.

In Column 18, Line 53, Change "dihydroxyphtalic," to --dihydroxyphthalic--.

In the Claims

In Column 77, Line 6, In Claim 13, Change "brevicompaetum." to --brevicompactum.--.

In Column 77, Line 8, In Claim 14, Change "brevicompaetum." to --brevicompactum.--.

This certificate supersedes the Certificate of Correction issued April 8, 2014.

Signed and Sealed this
Sixth Day of May, 2014

Michelle K. Lee
*Deputy Director of the United States Patent and Trademark Office*

SEQUENCE LISTING

<160> NUMBER OF SEQ ID NOS: 40

<210> SEQ ID NO 1
<211> LENGTH: 316
<212> TYPE: PRT
<213> ORGANISM: Penicillium brevicompactum

<400> SEQUENCE: 1

```
Met Ser Leu Phe Leu Leu Ala Leu Lys Gln Cys Val Thr Trp Ser Phe
1               5                   10                  15

Leu Ser Lys Ile Val Trp Ala Thr Leu Ile Ala Gly Ala Leu Lys Leu
            20                  25                  30

Gln Gln Asp Pro Glu Ser Leu Ser Ile Glu Phe Ile Leu Tyr Lys Ala
        35                  40                  45

Gly Leu Cys Phe Val His Cys Leu Leu Leu Cys Gly Ala Gly Asn Thr
    50                  55                  60

Trp Asn Asp Leu Val Asp Arg Asp Ile Asp Ala Arg Val Ala Arg Thr
65                  70                  75                  80

Lys Met Arg Pro Leu Ala Ser Gly Lys Val Thr Leu Thr Glu Ala Leu
                85                  90                  95

Leu Trp Met Thr Gly Gln Tyr Phe Leu Ser Val Lys Met Leu Asp Leu
            100                 105                 110
```

```
Ile Leu Asp Gly Arg Asn Ile Trp Ser Leu Met Leu Pro Leu Thr Ala
            115                 120                 125

Ser Ile Met Leu Tyr Pro Tyr Leu Lys Arg Pro Ile Phe Ser Lys Val
    130                 135                 140

Phe Val Tyr Pro Gln Tyr Ile Leu Gly Leu Ala Ile Gly Tyr Pro Ala
145                 150                 155                 160

Ile Thr Gly Trp Ala Ser Ile Thr Gly Ser Glu Glu Pro Leu Gly Asp
                165                 170                 175

Ile Ile Lys His Cys Ile Pro Ile Cys Leu Leu Val Phe Phe Trp Cys
            180                 185                 190

Val Tyr Phe Asn Thr Ala Tyr Ser His Gln Asp Ser Val Asp Asp Arg
    195                 200                 205

Lys Met Asn Ile Asn Ser Ala Tyr Val Ile Ala Gly Gln Arg Ile Arg
210                 215                 220

Leu Phe Leu Ala Phe Leu Ser Val Leu Pro Leu Leu Thr Ile Pro Tyr
225                 230                 235                 240

Ile Ile Ser Thr Ile Asn Ser Pro Trp Leu Trp Val Ser Trp Met Ala
                245                 250                 255

Thr Trp Thr Val Ser Ile Ile Met Gln Ile Ala Gln Phe Asp Ser Gln
            260                 265                 270

Lys Leu Glu Ser Gly Gly Arg Ile His Trp Asp Asn Phe Leu Leu Gly
    275                 280                 285

Leu Trp Thr Ile Ala Ala Cys Met Val Glu Val Gly Leu Gln Lys Val
290                 295                 300

Glu Phe Trp Lys Asn Val Glu Gly Tyr Ile Lys Leu
305                 310                 315

<210> SEQ ID NO 2
<211> LENGTH: 423
<212> TYPE: PRT
<213> ORGANISM: Penicillium brevicompactum

<400> SEQUENCE: 2

Met Ser Leu Pro Leu Pro Pro Ala Leu Ser Glu Leu Ala Arg Ala Leu
1               5                   10                  15

Pro Tyr Ser Arg Thr Gln Trp Leu Pro Ile Phe Val Gly Phe Leu Ile
            20                  25                  30

Gly Tyr Pro Ile Leu Ile Arg Ala Leu Arg Tyr Lys Arg His Gly Glu
        35                  40                  45

Met Lys Lys Lys Phe Tyr Phe Pro Thr Arg Glu Ser Met Ala Glu Met
50                  55                  60

Thr Asp Glu Glu Ala Phe Leu Ile Gln Lys Glu Met Ala Gln Leu Glu
65                  70                  75                  80

Phe Pro Phe Met Phe Leu Thr Ser Gly Gln Phe Ala Leu Phe Arg Thr
                85                  90                  95

Tyr Gly Ile Pro Thr Ile Ser His Leu Leu Thr Lys Thr Gly Gln Phe
            100                 105                 110

Ser Lys Pro Glu Thr Ser Phe Lys Arg Tyr Thr Asp Thr Ala Ala Leu
        115                 120                 125

Ile Gly Glu Met Val Glu Asn Ser Pro Thr Ser Gln Arg Ala Phe Ile
130                 135                 140

Ser Val Ala Arg Thr Arg Phe Leu His Ser Gly Tyr Gln Ala Ser Gly
145                 150                 155                 160

Lys Ile Leu Asp Ala Asp Leu Leu Tyr Thr Leu Ala Leu Phe Ala Val
                165                 170                 175
```

```
Gln Pro Val Arg Phe Ile Glu Asn Phe Glu Trp Arg Thr Leu Ser Asp
            180                 185                 190

Leu Glu Leu Cys Ala Ile Gly Thr Phe Trp Lys Ser Leu Gly Asp Ala
        195                 200                 205

Leu Gly Ile Ser Ser Glu Ile Leu Pro Ser Gly Lys Thr Gly Phe Lys
    210                 215                 220

Asp Gly Ile Gln Trp Leu Glu Val Asp Val Trp Ser Gln Asp Tyr
225                 230                 235                 240

Glu Ala Lys Tyr Met Val Pro Asp Pro Lys Asn Arg Glu Ser Ala Asp
                245                 250                 255

Gln Ala Thr Ala Val Leu Leu Tyr Asn Leu Pro Lys Phe Leu His Pro
            260                 265                 270

Ile Gly Leu Gln Phe Thr Ser Tyr Met Met Asp Arg Leu Arg Lys
        275                 280                 285

Ala Met Leu Tyr Glu Ala Pro Thr Pro Gly Trp Ser Met Val Phe Ser
    290                 295                 300

Thr Leu Leu Ala Ile Arg Lys Leu Ile Leu Arg Tyr Leu Ser Pro Pro
305                 310                 315                 320

Arg Pro Ala Ala Leu Ala Val Ser Asn Ile Ala Gln Lys Pro Asp Lys
                325                 330                 335

Asp Asp Arg Tyr His Arg Met Ser Trp Asp Ala Leu Pro Phe Tyr Ile
            340                 345                 350

Arg Pro Thr Phe Trp Asn Arg Trp Gly Pro Met Ala Trp Ile Ser Trp
        355                 360                 365

Leu Met Gly His Pro Val Pro Gly Asp Leu Gly Gln Lys Tyr Tyr Pro
    370                 375                 380

Gln Gly Tyr His Ile Gln Asp Ile Gly Pro Lys Tyr Phe Glu Gly Lys
385                 390                 395                 400

Gly His Lys Glu Ile Gln Glu Met Met Lys Glu Leu Lys Ile Ser Arg
                405                 410                 415

Thr Gly Lys Cys Pro Phe His
            420

<210> SEQ ID NO 3
<211> LENGTH: 2487
<212> TYPE: PRT
<213> ORGANISM: Penicillium brevicompactum

<400> SEQUENCE: 3

Met Asn Phe His Lys Gly Gln Pro Lys Glu Asp Leu Arg Val Leu Phe
1               5                   10                  15

Gly Pro Gln Cys Pro Asp Ile Thr Asp Ser Ile Thr His Ile Arg Asp
            20                  25                  30

Ala Ile Ser Lys Asp Pro Thr Gly Leu Gly Phe Leu Thr Asn Ile Leu
        35                  40                  45

Asp Glu Leu Pro Ser Leu Trp Pro Thr Ile Ala Gly Ala Trp Pro Ala
    50                  55                  60

Leu Lys Asn Val Glu Gly Glu Ser Gln Leu Leu Ala Leu Gly Arg Leu
65                  70                  75                  80

Phe Glu His Glu Ser Glu Asp Arg Val Glu Ala Ser Asn Leu Met Met
                85                  90                  95

Thr Pro Ile Thr Val Met Arg His Ile Val Asp Phe Trp Asn Leu Gln
            100                 105                 110

Asp Val Ala Thr His Pro Ala Phe Pro Ser Ser Ser Leu Ser Glu Thr
        115                 120                 125
```

-continued

```
Glu Met Pro Arg Ile Val Asp Thr Gln Gly Phe Cys Val Gly Leu Leu
    130                 135                 140
Ala Ala Ile Ala Val Ala Cys Ser Arg Asn Thr Gln Glu Phe Gln Tyr
145                 150                 155                 160
Val Ala Ser Asn Ala Ile Arg Leu Ser Leu Cys Val Gly Ala Leu Val
                165                 170                 175
Asp Leu Asp Glu Ile Leu Cys Gly Ser Thr Thr Ser Leu Ala Val Arg
            180                 185                 190
Trp Glu Ser Val Glu Asp Phe Asn His Leu Glu Lys Ile Leu Asn Asn
        195                 200                 205
Asn Pro Glu Gly Tyr Thr Ser Cys Tyr Thr Asp Val Lys Ser Val Thr
    210                 215                 220
Ile Thr Ile Pro Asn Asp Ser Ala Glu Arg Val Lys Gln Glu Ile His
225                 230                 235                 240
Asp His Gly Leu Arg Thr Lys Gln Leu Ser Leu Arg Gly Arg Phe His
                245                 250                 255
His Glu Ala His Arg Glu Gly Ile Gln His Ile Met Lys Leu Cys Thr
            260                 265                 270
Asn Asp Ser Arg Phe Lys Leu Pro Arg Ser Asp Ala Leu Leu Thr Pro
        275                 280                 285
Leu Arg Ser Ser Gln Gly Gly Glu Ile Phe Gln Gln Glu Ala Leu Leu
    290                 295                 300
His Thr Val Ala Leu Asp Ser Ile Leu Cys Ala Lys Ala Asn Trp Tyr
305                 310                 315                 320
Asp Val Val Ser Ala Leu Ile Asn Ser Thr Glu Met Thr Val Asp Gln
                325                 330                 335
Ser His Leu Leu Ser Ile Gly Pro Glu Glu Phe Val Pro Arg Ser Ala
            340                 345                 350
Arg Ser Arg Ser Val Ala Arg Arg Glu Leu Gln Ser Tyr Ala Met Gln
        355                 360                 365
Gly Phe Ser Asn Glu Ser Pro Gln Pro Ser Thr Ala Ser Leu Ser Asn
    370                 375                 380
Ser Val Gln Thr Phe Asp Ser Arg Pro Gln Ala Ala Glu Ala Ser Pro
385                 390                 395                 400
Ile Ala Ile Thr Gly Met Ala Cys Arg Tyr Pro Asn Ala Asp Thr Leu
                405                 410                 415
Ala Gln Leu Trp Asp Leu Leu Glu Leu Gly Arg Cys Thr Val Lys Ser
            420                 425                 430
Pro Pro Glu Ser Arg Phe His Met Ser Asp Leu Gln Arg Glu Pro Lys
        435                 440                 445
Gly Pro Phe Trp Gly His Phe Leu Glu Arg Pro Asp Val Phe Asp His
    450                 455                 460
Arg Phe Phe Asn Ile Ser Ala Arg Glu Ala Glu Ser Met Asp Pro Gln
465                 470                 475                 480
Gln Arg Val Ala Leu Gln Val Ala Tyr Glu Ala Met Glu Ser Ala Gly
                485                 490                 495
Tyr Leu Gly Trp Gln Pro Asn Gly Leu Ser Arg Asp Ile Gly Cys Tyr
            500                 505                 510
Val Gly Val Gly Ser Glu Asp Tyr Thr Glu Asn Val Ala Ser Arg Asn
        515                 520                 525
Ala Asn Ala Phe Ser Ile Thr Gly Thr Leu Gln Ser Phe Ile Ala Gly
    530                 535                 540
Arg Ile Ser His His Phe Gly Trp Ser Gly Pro Ser Ile Ser Leu Asp
```

```
                545                 550                 555                 560
            Thr Ala Cys Ser Ser Ala Ala Val Ala Ile His Leu Ala Cys Lys Ala
                        565                 570                 575
            Leu Gln Thr Asn Asp Cys Lys Ile Ala Leu Ala Gly Gly Val Asn Val
                        580                 585                 590
            Leu Thr Asn Pro Arg Val Tyr Gln Asn Leu Ser Ala Ala Ser Phe Leu
                        595                 600                 605
            Ser Pro Ser Gly Ala Cys Lys Pro Phe Asp Ala Ser Ala Asp Gly Tyr
                        610                 615                 620
            Cys Arg Gly Glu Gly Ala Gly Leu Phe Val Leu Arg Pro Leu Gln Asp
            625                 630                 635                 640
            Ala Ile Asp Asn Gly Asp Pro Ile Leu Gly Val Ile Ala Gly Ser Ala
                        645                 650                 655
            Val Asn Gln Gly Ser Asn Asn Ser Pro Ile Thr Val Pro Asp Ala Glu
                        660                 665                 670
            Ala Gln Arg Ser Leu Tyr Asn Lys Ala Met Ser Leu Ala Gly Val Ser
                        675                 680                 685
            Pro Asp Glu Val Thr Tyr Val Glu Ala His Gly Thr Gly Thr Gln Val
                        690                 695                 700
            Gly Asp Pro Ile Glu Leu Asp Ser Leu Arg Arg Thr Phe Gly Gly Pro
            705                 710                 715                 720
            Gln Arg Arg Asn Ser Leu His Ile Gly Ser Ile Lys Gly Asn Ile Gly
                        725                 730                 735
            His Thr Glu Thr Ser Ser Gly Ala Ala Gly Leu Leu Lys Thr Ile Leu
                        740                 745                 750
            Met Leu Gln Gln Gln Arg Ile Pro Arg Gln Ala Asn Phe Asn Gln Leu
                        755                 760                 765
            Asn Pro Lys Val Lys Ser Leu Thr Pro Asp Arg Leu Val Ile Ala Ser
                        770                 775                 780
            Glu Ser Thr Glu Trp Ala Ser Thr Glu Arg Val Ala Met Val Ser Asn
            785                 790                 795                 800
            Tyr Gly Ala Ser Gly Ser Asn Ala Ala Leu Ile Val Lys Glu His Ala
                        805                 810                 815
            Pro Ile Arg Ser Glu Gln Asn Gly Thr Ala Pro Glu Tyr Ile Gln Asn
                        820                 825                 830
            Val Pro Ile Leu Val Ser Ala Arg Ser Glu Glu Ser Leu Arg Ala Tyr
                        835                 840                 845
            Cys Gly Ala Leu Arg Ala Thr Leu Leu Ser His Pro Pro Ser Glu Thr
            850                 855                 860
            Leu Val Gln Lys Leu Ala Tyr Asn Leu Ala Met Lys Gln Asn Arg Asp
            865                 870                 875                 880
            Leu Pro Leu Asn Leu Thr Phe Ser Thr Ser Asp Ala Thr Ser Leu
                        885                 890                 895
            Ser Ala Arg Leu Glu Ala Ile Ser Thr Gly Ala Ser Ala Asp Leu Ile
                        900                 905                 910
            Gln Lys Arg Pro Ser Asn Glu Pro Pro Val Val Leu Cys Phe Gly Gly
                        915                 920                 925
            Gln Asn Gly Leu Thr Ala Thr Ile Ser Lys Glu Val Phe Asp Ala Ser
                        930                 935                 940
            Ala Leu Leu Arg Thr His Leu Glu Asp Cys Glu Glu Val Gly Arg Thr
            945                 950                 955                 960
            Leu Gly Leu Pro Ser Leu Phe Pro Thr Ile Phe Ser Ser Ala Pro Ile
                        965                 970                 975
```

-continued

Thr Asn Ile Ile His Leu His Phe Ile Leu Phe Ser Ile Gln Tyr Ala
                980                 985                 990

Ser Ala Lys Ala Trp Leu Asp Ser Gly Leu Arg Val Ser Arg Ile Val
        995                 1000                1005

Gly His Ser Phe Gly Gln Leu Thr Ala Leu Ser Val Ala Gly Ser
    1010                1015                1020

Leu Ser Val Arg Asp Gly Ile His Leu Val Thr Glu Arg Ala Arg
    1025                1030                1035

Leu Ile Glu Ser Ser Trp Gly Pro Glu Ser Gly Ile Met Leu Ala
    1040                1045                1050

Val Glu Gly Thr Asp Ile Glu Val Gln Gln Leu Leu Asp Gln Thr
    1055                1060                1065

Gly His Ile Ala Asp Val Ala Cys Tyr Asn Gly Pro Arg Gln Gln
    1070                1075                1080

Val Leu Ala Gly Thr Ala Glu Ser Ile Ala Ala Ile Glu Asn Ala
    1085                1090                1095

Ala Ala Arg Thr Pro Ser Ala Ser Lys Leu Arg Leu Thr Arg Leu
    1100                1105                1110

Gln Asn Ser His Ala Phe His Ser Arg Leu Val Asp Ser Ile Val
    1115                1120                1125

Pro Ala Ile Met Glu Val Ala Gly Ser Leu Val Tyr Gln Thr Pro
    1130                1135                1140

Ile Ile Pro Ile Glu Ala Cys Ser Ala Ser Gly Asp Trp Ser Thr
    1145                1150                1155

Ile Thr Ala Ala Glu Ile Val Glu His Ser Arg Met Pro Val Tyr
    1160                1165                1170

Phe Arg Arg Ala Val Glu Arg Val Ala Glu Lys Leu Gln Ala Pro
    1175                1180                1185

Ala Val Trp Leu Glu Ala Gly Ser Ala Ser Pro Ile Ile Pro Met
    1190                1195                1200

Val Arg Arg Val Leu Glu Ser Ser Ser Val Ala Asn Thr Tyr His
    1205                1210                1215

Lys Ile Asp Leu Gly Gly Ser Ser Gly Ala Gln Asn Leu Ala Asn
    1220                1225                1230

Val Thr Ser Ala Leu Trp Ala Gln Gly Val His Val Gln Phe Trp
    1235                1240                1245

Pro Phe Asp Arg Ala Gln His Gly Ser Phe Lys Trp Met Asn Leu
    1250                1255                1260

Pro Pro Tyr Gln Phe Ala Gln Asn Ser His Trp Val Asp Phe Asp
    1265                1270                1275

Pro Ala Ala Phe Ser Ser Ala Gly Pro Ser Ser Gly Lys Gln Ser
    1280                1285                1290

Ala Gly Gln Glu Ala Gly Leu Leu Cys Gln Leu Ser Glu Ser Pro
    1295                1300                1305

Asp Glu Arg Leu Tyr His Val Asn Ile Gln Asp Ala Leu Tyr Arg
    1310                1315                1320

Ala Cys Thr Gln Gly His Ala Val Leu Asn Gln Thr Leu Cys Pro
    1325                1330                1335

Ala Ser Met Tyr Met Glu Met Val Leu Arg Ala Ala Ala Ser Ile
    1340                1345                1350

Phe Pro Thr Gly Asn Ala Ser Glu Pro Ala Met Ser His Ile Glu
    1355                1360                1365

Asp Leu Thr Ile Ser Ser Pro Leu Val Leu Asp Pro Gln Gly Asp
    1370                1375                1380

```
Val Phe Leu Arg Leu Thr Ser Asp Gly Ala Gly Pro Thr Arg Pro
    1385                1390                1395

Trp Leu Phe Ser Ile Phe Ser Ser Glu Ser Asn Asp His Thr Ser
    1400                1405                1410

Val His Ala Glu Gly Thr Val Cys Leu His Gln Glu Arg Ser Arg
    1415                1420                1425

Ala Leu Ala Arg Phe Gln Ser Met Asp Arg Leu Leu Asp Ser Ala
    1430                1435                1440

Arg Ser Lys Thr Ile Glu Ala Asp Pro Ala Ser Asn Gly Leu Lys
    1445                1450                1455

Gly Ser Thr Val Tyr Ala Ala Leu Glu Ser Val Thr Asn Tyr Gly
    1460                1465                1470

Asp Tyr Phe Arg Gly Val Lys Lys Val Phe Ala Asn Gly Arg Glu
    1475                1480                1485

Ala Ser Gly Leu Val Ser Met Met Pro Ser Ala Ser Glu Thr Asn
    1490                1495                1500

Cys Asp Pro Ile Leu Leu Asp Asn Phe Leu Gln Val Ala Gly Ile
    1505                1510                1515

His Val Asn Cys Leu Ser Asp Arg Arg Ser Ser Glu Val Phe Val
    1520                1525                1530

Cys Asn Ala Ile Gly Glu Thr Phe Val Ile Asn Ser Leu Leu Lys
    1535                1540                1545

Gln Lys Asn Gly Ala Ser Pro Ser Thr Trp Lys Val Tyr Thr Ser
    1550                1555                1560

Tyr Val Arg Pro Ser Lys Thr Glu Ile Ala Cys Asp Ile Tyr Val
    1565                1570                1575

Met Asp Cys Gln Thr Asp Thr Leu Ser Ala Ala Met Met Gly Val
    1580                1585                1590

Arg Phe Thr Ser Val Ser Ile Arg Ser Leu Thr Arg Ala Leu Ala
    1595                1600                1605

Lys Leu Asn Asn Asn Val Leu Glu Thr Ala Glu Ala Gln Ser Val
    1610                1615                1620

Val Glu Pro Ala Ile Pro Ala Glu Lys Ser Val Val Thr Ala Thr
    1625                1630                1635

Pro Ser Ala Pro Ala Ala Asp Gly Gly Gly Ala Lys Asp Leu Ala
    1640                1645                1650

Thr Val Gln Glu Met Leu Cys Glu Leu Phe Gly Val Ser Val Ala
    1655                1660                1665

Glu Val Ser Pro Ser Val Ser Leu Val Asp Ile Gly Val Asp Ser
    1670                1675                1680

Leu Met Ser Thr Glu Val Leu Ser Glu Ile Lys Lys Arg Phe Gln
    1685                1690                1695

Val Asp Met Ser Tyr Thr Thr Leu Val Asp Ile Pro Asn Ile Gln
    1700                1705                1710

Gly Leu Val Glu His Ile Phe Pro Gly His Ser His Ala Ala Pro
    1715                1720                1725

Ser Gln Pro Val Val Glu Thr Ala Pro Val Gln Ser Val Ala Pro
    1730                1735                1740

Gln Ala Val Ser His Val Pro Thr Pro Ala Asn Asn Gly Pro Pro
    1745                1750                1755

Leu Val Ser Val Ala Arg Gln Cys Phe Asp Thr Thr His Ala Ala
    1760                1765                1770

Val Ser His Thr Ser Asp Ala His Trp Thr Gly Phe Phe His Thr
```

|  |  |  |
| --- | --- | --- |
| 1775 | 1780 | 1785 |

Thr Tyr Pro Lys Gln Met Thr Leu Leu Thr Ala Tyr Ile Leu Glu
    1790                     1795                     1800

Ala Phe Arg Ala Leu Gly Ser Pro Leu Glu Ala Ser Glu Pro Asn
    1805                     1810                     1815

Glu Val Leu Ile Pro Ile Ser Val Leu Pro Arg His Glu Gln Leu
    1820                     1825                     1830

Arg Lys His Leu Tyr Lys Ile Leu Glu Ser Val Gly Leu Val Arg
    1835                     1840                     1845

Gln Met Pro Thr Gly Glu Leu Val Arg Thr Thr Thr Pro Ile Pro
    1850                     1855                     1860

Leu Ser Gln Ser His Asp Leu His Thr Gln Ile Arg Ala Glu Tyr
    1865                     1870                     1875

Pro Pro Tyr Ala Leu Glu His Asp Leu Leu Gln Ile Thr Ala Pro
    1880                     1885                     1890

Arg Leu Ala Asp Cys Leu Thr Gly Lys Ala Asp Gly Val Ser Leu
    1895                     1900                     1905

Ile Phe Gln Asp Ala Asn Thr Arg Arg Leu Val Gly Asp Val Tyr
    1910                     1915                     1920

Ala Gln Ser Pro Val Phe Lys Ser Gly Asn Leu Tyr Leu Ala Arg
    1925                     1930                     1935

Tyr Leu Leu Asp Val Val Gln Ser Phe Gly Ser Ser Arg Thr Ile
    1940                     1945                     1950

Lys Ile Leu Glu Ile Gly Ala Gly Thr Gly Gly Thr Thr Lys Asn
    1955                     1960                     1965

Leu Leu Glu Lys Leu Ser Thr Ile Pro Gly Leu Ser Thr Arg Leu
    1970                     1975                     1980

Glu Tyr Thr Phe Thr Asp Ile Ser Pro Ser Leu Val Ala Ala Gly
    1985                     1990                     1995

Arg Lys Thr Phe Ala Asn Tyr Asn Phe Met Arg Tyr Glu Thr Leu
    2000                     2005                     2010

Asn Val Glu Asn Asp Pro Pro Ser Ala Leu Ser Gly Gln Tyr Asp
    2015                     2020                     2025

Ile Val Leu Ser Thr Asn Cys Val His Ala Thr Arg Asn Leu Arg
    2030                     2035                     2040

Glu Ser Cys Thr Asn Ile Arg Lys Leu Leu Arg Pro Asp Gly Ile
    2045                     2050                     2055

Leu Cys Leu Val Glu Leu Thr Arg Asp Ile Phe Trp Leu Asp Leu
    2060                     2065                     2070

Val Phe Gly Leu Leu Glu Gly Trp Trp Arg Phe Glu Asp Gly Arg
    2075                     2080                     2085

Glu His Ala Leu Ala Thr Glu Met Met Trp Asp Gln Thr Leu Arg
    2090                     2095                     2100

Gln Ser Gly Phe Glu Trp Val Asp Trp Thr Asn Asn Glu Thr Val
    2105                     2110                     2115

Glu Ser Asn Ala Leu Arg Val Ile Val Ala Ser Pro Thr Gly Asn
    2120                     2125                     2130

Ser Ser Thr Ala Thr Met Ser Pro Ser Lys Leu Thr Lys Met Glu
    2135                     2140                     2145

Thr Val Val Trp Gly Glu Arg Asp Asn Leu Gln Leu Arg Ala Asp
    2150                     2155                     2160

Ile Tyr Tyr Pro Glu Thr Val Asp Thr Thr Arg Lys Gln Arg Pro
    2165                     2170                     2175

-continued

```
Ile Ala Leu Met Ile His Gly Gly His Val Met Leu Ser Arg
    2180            2185                2190

Lys Asp Ile Arg Pro Ala Gln Thr Gln Thr Leu Leu Asp Ala Gly
2195                2200                2205

Phe Leu Pro Val Ser Ile Asp Tyr Arg Leu Cys Pro Glu Val Ser
2210                2215                2220

Leu Ala Glu Gly Pro Met Ala Asp Ala Arg Asp Ala Leu Ser Trp
2225                2230                2235

Val Arg Arg Val Leu Pro Asn Ile Pro Leu Leu Arg Ala Asp Ile
2240                2245                2250

Arg Pro Asp Gly Asn Gln Val Val Ala Ile Gly Trp Ser Thr Gly
2255                2260                2265

Gly His Leu Ala Met Thr Leu Pro Phe Thr Ala Pro Ala Ala Gly
2270                2275                2280

Ile Ser Ala Pro Asn Ala Val Leu Ala Phe Tyr Cys Pro Thr Asn
2285                2290                2295

Tyr Glu Asp Pro Phe Trp Ser Asn Pro Asn Phe Pro Phe Gly Gln
2300                2305                2310

Thr Val Ala Ser Asn Glu Met Glu Tyr Asp Val Trp Glu Gly Leu
2315                2320                2325

Gln Ser Met Pro Ile Ala Gly Tyr Asn Pro Ala Leu Lys Glu Arg
2330                2335                2340

Pro Leu Gly Gly Trp Met Ser Thr Arg Asp Pro Arg Ser Arg Ile
2345                2350                2355

Ala Leu His Met Asn Trp Thr Gly Gln Thr Leu Pro Val Leu Leu
2360                2365                2370

Lys Ala Cys Thr Ile Lys Gly Asn Thr Glu Lys Cys Ser Pro Asp
2375                2380                2385

Asp Leu Ser Arg Pro Thr Glu Glu Ile Gln Ala Val Ser Pro
2390                2395                2400

Asn Tyr Gln Ile Arg Val Gly Arg Tyr Asn Thr Pro Thr Phe Leu
2405                2410                2415

Ile His Gly Thr Ser Asp Asp Leu Val Pro Cys Ala Gln Thr Glu
2420                2425                2430

Ser Thr His Gly Ala Leu Thr Ala Ser Gly Val Glu Ala Glu Leu
2435                2440                2445

Arg Val Val Gln Glu Ala Ala His Leu Phe Asp Leu Tyr Pro Ala
2450                2455                2460

Ser His Ala Gly Gln Glu Ala Lys Ala Ala Val Ala Glu Gly Tyr
2465                2470                2475

Glu Phe Leu Arg Arg His Val Gln Leu
2480                2485
```

<210> SEQ ID NO 4
<211> LENGTH: 535
<212> TYPE: PRT
<213> ORGANISM: Penicillium brevicompactum

<400> SEQUENCE: 4

```
Met Lys Ser Leu Ser Leu Thr Trp Ile Thr Ala Val Ala Val Leu
1               5                   10                  15

Tyr Leu Val Gln Arg Tyr Val Arg Ser Tyr Trp Arg Leu Lys Asp Ile
                20                  25                  30

Pro Gly Pro Val Leu Ala Lys Leu Thr Asp Leu Gln Arg Val Trp Trp
            35                  40                  45
```

-continued

```
Val Lys Thr Gly Arg Ala His Glu Phe His Arg Asp Met His Ala Met
 50                  55                  60
Tyr Gly Pro Ile Val Arg Phe Gly Pro Asn Met Val Ser Val Ser Asp
 65                  70                  75                  80
Pro Arg Val Ile Pro Thr Ile Tyr Pro Ser Arg Pro Gly Phe Pro Lys
                 85                  90                  95
Gly Asp Phe Tyr Arg Thr Gln Lys Pro Tyr Thr Arg Asn Lys Gly Ala
                100                 105                 110
Met Pro Ala Val Phe Asn Thr Gln Asp Glu Asp Leu His Lys Gln Leu
                115                 120                 125
Arg Ser Pro Ile Ala Ser Leu Tyr Ser Met Thr Asn Val Val Arg Leu
130                 135                 140
Glu Pro Leu Val Asp Glu Thr Leu Thr Val Leu Ser Lys Gln Leu Asp
145                 150                 155                 160
Glu Arg Phe Val Gly Thr Asn Asp Lys Pro Phe Asp Leu Gly Asp Trp
                165                 170                 175
Leu Gln Tyr Phe Ala Phe Asp Ser Met Gly Thr Leu Thr Phe Ser Arg
                180                 185                 190
Arg Tyr Gly Phe Leu Glu Gln Gly Arg Asp Met His Gly Ile Leu Gln
                195                 200                 205
Glu Ile Trp Asn Phe Met Thr Arg Val Ala Val Met Gly Gln Ile Pro
210                 215                 220
Trp Phe Asp Glu Ile Trp Asn Lys Asn Ser Phe Ile Thr Leu Phe Lys
225                 230                 235                 240
Arg Pro Thr Gly Phe Gly Val Leu Lys Val Val Asp Asn Phe Ile Ser
                245                 250                 255
Gln Arg Val Ser Ser Arg Glu Asn Asp Glu Lys Ala Asp Glu Lys Asp
                260                 265                 270
Met Leu Ser Gln Phe Leu Asp Ile Gln Ala Ser Asn Pro His Ser Ile
                275                 280                 285
Met Pro Trp Ala Pro Arg Ala Trp Thr Phe Ser Asn Val Met Ala Gly
290                 295                 300
Ser Asp Ser Thr Ala Asn Val Met Arg Thr Met Met Tyr Asn Leu Leu
305                 310                 315                 320
Val Asp Arg Asp Thr Leu Arg Ser Leu Arg Ala Glu Leu Leu Glu Ala
                325                 330                 335
Glu Asn Ser Asn Gly Leu Ser Arg Ser Leu Pro Ser Trp Asp Gly Val
                340                 345                 350
Arg Ser Leu Pro Tyr Leu Asp Ala Cys Val Leu Glu Ala Leu Arg Leu
                355                 360                 365
His Pro Pro Phe Cys Leu Pro Phe Glu Arg Val Val Pro Glu Gly Gly
                370                 375                 380
Ile Thr Val Cys Glu Thr Tyr Leu Pro Ala Gly Thr Val Val Gly Ile
385                 390                 395                 400
Ser Pro Tyr Leu Ala Asn Arg Asp Lys Gln Thr Phe Gly Asp Asp Ala
                405                 410                 415
Asp Lys Trp Arg Pro Ser Arg Trp Leu Asp Leu Ser Arg Glu Asp Arg
                420                 425                 430
Val Lys Leu Glu Asn Ser Ile Leu Thr Phe Gly Ala Gly Arg Arg Thr
                435                 440                 445
Cys Leu Gly Lys Asn Ile Ala Ile Leu Glu Ile Lys Lys Leu Phe Pro
                450                 455                 460
Met Leu Leu Leu Asn Tyr Glu Ile Glu Ile Val Asn Pro Glu Asn Tyr
465                 470                 475                 480
```

```
Gln Thr Thr Asn Ala Trp Phe Arg Gln Trp Gly Leu Gln Ala Val
                485                 490                 495

Ile Arg Lys Leu Pro Ala Pro Glu Arg Asp Asp Thr Ile Glu Gln Lys
            500                 505                 510

Ala Ser Ile Pro Pro Ala Leu Asn Ile Pro Pro Ser Ser Ser Thr Val
            515                 520                 525

Glu Val Arg Ile Ile Asp Ser
            530                 535

<210> SEQ ID NO 5
<211> LENGTH: 261
<212> TYPE: PRT
<213> ORGANISM: Penicillium brevicompactum

<400> SEQUENCE: 5

Met Ile Lys Ser Gln Thr Val Ile Gln Glu Pro Arg Asn Ile Ser Asp
1               5                   10                  15

Val Leu Asp Ser Asp Glu Ser Ser Leu Gly Val Arg Ser Lys Asp Ile
            20                  25                  30

Glu Ala Ile Ile Trp Ser His Ala His Phe Asp His Ile Gly Asp Pro
        35                  40                  45

Ser Thr Phe Pro Pro Ser Thr Glu Leu Val Val Gly Pro Gly Ile Arg
    50                  55                  60

Asp Thr His Trp Pro Gly Phe Pro Thr Asn Pro Asp Ala Ile Asn Leu
65                  70                  75                  80

Asn Thr Asp Ile Gln Gly Arg Asn Val Arg Glu Ile Ser Phe Glu Lys
                85                  90                  95

Thr Gln Lys Gly Ala Thr Lys Ile Gly Ser Phe Asp Ala Val Asp Tyr
            100                 105                 110

Phe Gly Asp Gly Ser Phe Tyr Leu Leu Asp Ala Ala Gly His Ser Val
        115                 120                 125

Gly His Ile Gly Ala Leu Ala Arg Val Thr Thr Ser Pro Val Ser Phe
    130                 135                 140

Val Phe Met Gly Gly Asp Ser Cys His His Ala Gly Val Leu Arg Pro
145                 150                 155                 160

Thr Lys Tyr Leu Pro Cys Pro Leu Asp Ser Gly Asp Thr Ser Leu Pro
                165                 170                 175

Cys Lys Ser Asp Ser Val Phe Thr Leu Ser Pro Ala Leu Pro Thr Asp
            180                 185                 190

Tyr Thr Ala Ala Leu Arg Thr Val Glu Asn Ile Lys Glu Leu Asp Ala
        195                 200                 205

Cys Glu Asp Val Phe Val Val Leu Ala His Asp Ala Thr Leu Lys Gly
    210                 215                 220

Lys Val Asp Phe Tyr Pro Ser Lys Ile Asn Asp Trp Lys Ala Lys Glu
225                 230                 235                 240

Tyr Gly Lys Lys Thr Lys Trp Leu Phe Tyr Lys Asp Ile Glu Asn Ser
                245                 250                 255

Ile Glu Gly Gln Lys
            260

<210> SEQ ID NO 6
<211> LENGTH: 527
<212> TYPE: PRT
<213> ORGANISM: Penicillium brevicompactum

<400> SEQUENCE: 6
```

-continued

```
Met Val Glu Ile Leu Asp Tyr Thr Lys Ala Leu Glu Val Leu Lys Glu
1               5                   10                  15
Tyr Pro Ser Gly Asp Gly Leu His Val Asp Thr Leu Leu Asp Ser Asp
            20                  25                  30
Asn His Gly Ala Leu Thr Tyr Asn Asp Phe Leu Ile Leu Pro Gly Ser
        35                  40                  45
Ile Thr Phe Ser Ala Ala Asp Val Ser Leu Asp Thr Lys Val Thr Arg
    50                  55                  60
Arg Phe Thr Ile Lys Ala Pro Leu Leu Ser Ser Pro Met Asp Thr Val
65                  70                  75                  80
Thr Glu His Asn Met Ala Ile His Met Ala Leu Leu Gly Gly Leu Gly
                85                  90                  95
Val Ile His Asn Asn Cys Pro Pro Asp Asp Gln Ala Glu Met Val Arg
            100                 105                 110
Lys Val Lys Arg Tyr Glu Asn Gly Phe Ile Leu Asp Pro Val Val Leu
        115                 120                 125
Ser Pro Ser Thr Thr Val Ala Glu Ala Lys Glu Leu Lys Thr Lys Trp
    130                 135                 140
Asn Phe Gly Gly Phe Pro Val Thr Glu Lys Gly Thr Leu His Ser Lys
145                 150                 155                 160
Leu Leu Gly Ile Val Thr Ser Arg Asp Ile Gln Phe His Lys Thr Pro
                165                 170                 175
Glu Asp Pro Val Thr Ala Val Met Ser Thr Asp Leu Val Thr Ala Pro
            180                 185                 190
Ala Gly Thr Thr Leu Ala Glu Ala Asn Glu Val Leu Arg Ser Ser Lys
        195                 200                 205
Lys Gly Lys Leu Pro Ile Val Asp Lys Asp Gly Leu Leu Val Ser Leu
    210                 215                 220
Leu Ser Arg Ser Asp Leu Met Lys Asn Ile His Tyr Pro Leu Ala Ser
225                 230                 235                 240
Lys Leu Pro Ser Lys Gln Leu Leu Cys Ala Ala Ile Ser Thr His
                245                 250                 255
Asp Ala Asp Lys Val Arg Leu Gln Lys Leu Val Asp Ala Gly Leu Asp
            260                 265                 270
Ile Val Val Asp Ser Ser Gln Gly Asn Ser Met Tyr Gln Ile Ala
        275                 280                 285
Met Ile Lys Trp Ile Lys Ser Thr Phe Pro Asp Ile Asp Ile Ala
    290                 295                 300
Gly Asn Ile Val Thr Arg Glu Gln Ala Ala Leu Ile Ala Ala Gly
305                 310                 315                 320
Ala Asp Gly Leu Arg Ile Gly Met Gly Ser Gly Ser Ala Cys Ile Thr
                325                 330                 335
Gln Glu Val Met Ala Val Gly Arg Pro Gln Ala Ala Ser Val Arg Ser
            340                 345                 350
Val Ser Ala Phe Ala Ala Arg Phe Gly Val Pro Thr Ile Ala Asp Gly
        355                 360                 365
Gly Val Gln Asn Leu Gly His Ile Val Lys Gly Leu Ala Leu Gly Ala
    370                 375                 380
Ser Ala Val Met Met Gly Ser Leu Leu Ala Gly Thr Thr Glu Ser Pro
385                 390                 395                 400
Gly Glu Tyr Tyr Val Ser Asn Glu Gly Gln Leu Val Lys Ala Phe Arg
                405                 410                 415
Gly Met Gly Ser Ile Ala Val Met Glu Asp Lys Gly Lys Ser Gly Gly
            420                 425                 430
```

Gly Lys Asn Ala Gly Ala Ser Arg Tyr Phe Ser Glu Asn Asp Lys Val
                435                 440                 445

Lys Val Ala Gln Gly Val Ala Gly Ser Val Val Asp Arg Gly Ser Ile
    450                 455                 460

Thr Gln Tyr Val Pro Tyr Leu Val Ala Gly Ile Gln His Ser Leu Gln
465                 470                 475                 480

Asp Ile Gly Val Gln Asp Leu Glu Ala Leu His Thr Gly Val Asn Asn
                485                 490                 495

Gly Gln Val Arg Phe Glu Met Arg Ser Ala Ser Ala Gln Thr Glu Gly
                500                 505                 510

Asn Val His Gly Leu His Ser His Glu Lys Lys Leu Tyr Ser Ser
                515                 520                 525

<210> SEQ ID NO 7
<211> LENGTH: 398
<212> TYPE: PRT
<213> ORGANISM: Penicillium brevicompactum

<400> SEQUENCE: 7

Met Ser Ala Ala Ser Pro Ala Ser Ile Ile Gln Glu Leu Ala Ser Ala
1               5                   10                  15

Ala Lys Gln Tyr Glu Asn Asn Glu Ser Gly Ala Arg Glu Ala Leu Ile
                20                  25                  30

Ala Gln Ser Arg Ala Leu Ile Ala Ser Leu Glu Val Pro Ser Glu Phe
            35                  40                  45

Ile Gln His Thr Phe Trp Ser Gln Pro Ala Leu Ser Ala Ile Val Arg
50                  55                  60

Leu Ala Thr Asp Val Asn Leu Phe Gln Tyr Leu Lys Asp Ala Gln Glu
65                  70                  75                  80

Glu Gly Leu Ser Ala Glu Ala Leu Ala Ser Lys Thr Gly Met Asp Val
                85                  90                  95

Ser Leu Phe Ala Arg Leu Ala Arg His Leu Val Ala Met Asn Val Ile
                100                 105                 110

Thr Ser Arg Asn Gly Val Phe Tyr Gly Thr Ala Leu Ser Asn Gly Leu
            115                 120                 125

Ala Ala Glu Asn Tyr Gln Gln Ser Ile Arg Phe Cys His Asp Val Ser
130                 135                 140

Arg Pro Ser Phe Gly Ala Phe Pro Ser Phe Pro Lys Gly Asn Gly Tyr
145                 150                 155                 160

Lys Thr Pro Ala Leu Gly Thr Thr Asp Gly Pro Phe Gln Ser Ala His
                165                 170                 175

Lys Val Asp Ile Ser Phe Pro Gln Trp Leu Val Gly Asn Pro Pro Tyr
                180                 185                 190

Leu Gln Tyr Phe Asn Ser Tyr Met Ser Ala Tyr Arg Ala Gly Lys Pro
            195                 200                 205

Asn Trp Cys Asp Asn Gly Phe Tyr Pro Val Ala Asp Arg Leu Leu Asn
210                 215                 220

Gly Phe Asp Ala Ser Val Ser Asp Val Leu Leu Val Asp Val Gly Gly
225                 230                 235                 240

Gly Arg Gly His Asp Ile Ala Thr Phe Gly Ser Gln Phe Ser Pro Leu
                245                 250                 255

Pro Gly Arg Leu Val Leu Gln Asp Arg Glu Gln Val Ile Asn Ser Ile
                260                 265                 270

Pro Ala Asp Glu Ser Arg Gln Phe Glu Ala Thr Thr His Asp Ile Phe
            275                 280                 285

Thr Thr Gln Pro Val Lys Asn Ala Arg Ala Tyr Tyr Met His Ser Val
    290                 295                 300

Pro His Gly Phe Gly Asp Glu Asp Ala Val Lys Ile Met Ala Asn Leu
305                 310                 315                 320

Val Pro Ala Leu Ala Lys Gly Tyr Ser Arg Val Leu Leu Asn Glu Ile
                325                 330                 335

Val Val Asp Glu Glu Ser Pro Val Met Ser Ala Thr Asn Met Asp Leu
            340                 345                 350

Ile Met Leu Ala His Met Gly Ala Lys Glu Arg Thr Glu Ala Asp Trp
        355                 360                 365

Arg Ser Ile Leu Thr Arg Ala Gly Leu Lys Val Val Asn Ile Tyr Ser
    370                 375                 380

Tyr Pro Gly Val Ala Glu Ser Leu Ile Glu Ala Glu Leu Ala
385                 390                 395

<210> SEQ ID NO 8
<211> LENGTH: 433
<212> TYPE: PRT
<213> ORGANISM: Penicillium brevicompactum

<400> SEQUENCE: 8

Met Ser Thr Glu Lys Phe Thr Ile Thr Glu His Leu Val Pro Gly Ser
1               5                   10                  15

His Ile Arg Glu Tyr Pro Gly Ser Thr Val Asn Gln Gln Asp Val Leu
            20                  25                  30

Lys Ile His Val Lys Asn Tyr Thr Pro Lys Arg Glu Gly Pro Val Pro
        35                  40                  45

Asp Asp Ala Ile Thr Phe Ile Ala Thr His Gly Val Gly Leu Pro Lys
    50                  55                  60

Glu Leu Tyr Glu Pro Leu Trp Asp Glu Leu Leu Asp Gln Ala Ser Gly
65                  70                  75                  80

Phe His Ile Arg Ala Ile Trp Met Ala Asp Val Ala Ser Met Asn Gln
                85                  90                  95

Ser Gly Ile His Asn Glu Asp Lys Leu Ser Met Asp Cys Ser Trp Met
            100                 105                 110

Asp His Ala Arg Asp Leu Leu Leu Met Ile Asn His Phe Arg Asp Gln
        115                 120                 125

Met Pro Arg Pro Leu Val Gly Ile Gly His Ser Phe Gly Gly Asn Ile
    130                 135                 140

Ile Thr Asn Leu Ala Tyr Leu His Pro Arg Leu Phe Thr Thr Leu Leu
145                 150                 155                 160

Leu Leu Asp Pro Leu Ile Gln Leu Ser Pro Pro Ser Leu Gly Phe Gly
                165                 170                 175

Thr Asp Ala Pro Ser Ala Ile Asn Tyr Thr Leu Trp Arg Asp Asp Val
            180                 185                 190

Trp Pro Ser Arg Glu Glu Ala Ile Arg Ala Asn Arg Ala Ile Met Gln
        195                 200                 205

Gly Met Asp Pro Arg Cys Leu Asp Arg Met Thr Lys His Phe Phe Arg
    210                 215                 220

Asp Leu Pro Thr Pro Leu Tyr Pro Asp Val Glu Ala Ile Lys Ala Arg
225                 230                 235                 240

Phe Gly Thr Thr Ala Asp Ser Thr Thr Thr Pro Val Thr Leu Thr Thr
                245                 250                 255

Pro Lys Tyr His Glu Leu Val Ala Gln Ile Arg Gln Asn Phe Asn Ala
            260                 265                 270

Arg Asp Pro Lys Thr Gly Arg Ile Glu Val Pro Arg Asp Thr His Ala
              275                 280                 285

Asp Met Asp Pro Leu Val Ala Tyr Ile Pro Leu Tyr Arg Pro Glu Pro
        290                 295                 300

Arg Ser Thr Phe Arg Arg Leu Glu Thr Leu Arg Pro Ser Cys Leu Trp
305                 310                 315                 320

Val Ile Ala Gly Ala Thr Phe Leu Asn Ile Asp Glu Ile Arg Glu Gly
                325                 330                 335

Val Lys Ile Cys Gly Ser Gly Ile Gly Gly Ser Gly Val Pro Asp
            340                 345                 350

Gly Arg Val Arg Glu Val Val Leu Pro Gly Phe Gly His Leu Met Pro
            355                 360                 365

Phe Gln Glu Val Lys Thr Val Ala Gly Thr Cys Val Val Trp Leu Gln
            370                 375                 380

Gln Glu Met Asp Arg Phe Arg Gln Thr Glu Arg Gln Trp Lys Glu Asp
385                 390                 395                 400

Arg Asp Gly Lys Ser His Gln Ala Val Glu Glu Asn Trp Tyr Lys Val
                405                 410                 415

Leu Lys Pro Ile Pro Thr Gly Arg Lys Lys Arg Ser Asp Lys Gly Lys
            420                 425                 430

Leu

<210> SEQ ID NO 9
<211> LENGTH: 948
<212> TYPE: DNA
<213> ORGANISM: Penicillium brevicompactum

<400> SEQUENCE: 9
atgtccctat tcctgctagc tttaaagcaa tgcgtaacgt ggagcttttt gagcaaaata      60
gtatgggcca ctttaatcgc cggcgctctc aaattacaac aggatccaga aagcctctcg     120
atcgagttca ttttgtacaa ggccggtctc tgtttcgtcc actgtctgct gctttgcggt     180
gccggaaaca catggaacga tcttgtggat cgcgatattg acgccagagt ggcacgcaca     240
aagatgcggc ctttggcatc tggaaaggtc actctgactg aggcacttct ttggatgacc     300
ggtcaatatt tcctgtccgt caaaatgctg gatctcattt tggatggacg aaacatctgg     360
agcctcatgc tgccattgac cgccagcatc atgctttacc cctacctgaa gcgacccatc     420
ttcagcaagg tcttcgttta cccccaatat atcctgggtc ttgctattgg ttaccccgcc     480
atcacaggt gggcttcgat caccggcagc gaggagcccc ttggtgacat catcaagcat     540
tgcatcccaa tctgcctcct tgtcttcttc tggtgtgtgt acttcaacac cgcatacagc     600
caccaagata gcgtcgatga ccggaagatg aacatcaact ctgcctacgt cattgcaggt     660
cagcgcattc gactgttcct tgccttttg agtgttctgc cacttcttac aattccatac     720
atcatctcta ccatcaactc gccgtggttg tgggtctcct ggatggctac ctggactgtt     780
tccatcatca tgcagattgc tcagtttgat tcgcagaagc ttgaaagtgg cggtcgtatc     840
cattgggaca acttcctgct gggattgtgg acgatcgctg cttgcatggt tgaagtcgga     900
ttgcagaagg tggaattctg gaagaatgtt gagggttaca ttaagctt                  948

<210> SEQ ID NO 10
<211> LENGTH: 1269
<212> TYPE: DNA
<213> ORGANISM: Penicillium brevicompactum

<400> SEQUENCE: 10

```
atgtctttgc ctttgcctcc agcactttct gagcttgcga gggcacttcc ctacagcaga      60
actcaatggc ttccaatctt cgtgggattt ctgattgggt accccatcct tatcagggca     120
ttgcgtttata agcgacatgg agagatgaag aagaaattct atttcccaac tcgcgagtcc    180
atggctgaaa tgaccgatga ggaggcattc ctgattcaaa aggaaatggc acagctcgag     240
ttcccattca tgttcttgac atctgggcag tttgcactat tccggacata tggcattccg     300
acaatctctc atcttctaac gaaaaccggg caattctcca agccagaaac atccttcaaa     360
cgctatacag acacagctgc tctgattggt gaaatggtag agaatagtcc tacctcgcag     420
agggcattca tctcagtagc ccgcacacga ttcctacata gcggctatca agcttcgggc     480
aagatcctcg atgctgattt gctttacacc cttgcactct ttgcggtcca gcctgtgcga    540
tttattgaga atttcgaatg gcggaccctg agtgatttgg aactctgtgc cattgggacc    600
ttttggaaga gtctaggtga tgctttgggt attagctctg agattcttcc atcgggcaag    660
acaggcttca aagatggtat ccaatggctt gaagaggtga tgtttggag tcaggattat     720
gaggccaagt acatggtccc agatcccaag aatcgcgagt cggcagatca agcgacggca    780
gttctacttt acaatctgcc aaaatttttg catccaatag gactgcaatt tacatcttat    840
atgatggatg atcggctgag gaaggcgatg ctgtatgaag ccccaactcc tggctggagc    900
atggttttct caaccctctt ggctattcgc aagttgattc tgcgttacct atcaccacca    960
cggcctgcgg ctcttgcggt gtcaaacata gctcaaaagc ccgacaaaga tgatcgctat   1020
caccgcatgt cttgggatgc actcccattt tacatcaggc ctactttctg gaacagatgg   1080
ggtccaatgg cgtggatctc ttggttgatg gccaccctg tcccaggcga tcttggccag    1140
aagtactatc acagggata tcatatacaa gatattggac caaaatactt tgaaggaaag    1200
ggccacaagg agatccagga aatgatgaag gaattaaaga tctcaaggac ggggaaatgt   1260
cccttccat                                                            1269

<210> SEQ ID NO 11
<211> LENGTH: 7461
<212> TYPE: DNA
<213> ORGANISM: Penicillium brevicompactum

<400> SEQUENCE: 11
atgaatttcc acaaagggca accgaaggaa gatcttcggg tcctctttgg accacaatgc    60
ccggacatca cagattctat cactcacata cgagatgcca tatccaaaga tcccacaggt   120
ttgggatttc tcacaaatat tctcgacgaa ttaccctcct tatggccaac aatcgccggt   180
gcctggccag ccttgaagaa tgtcgaaggc gagagtcaac tgcttgcact cggccgcctt   240
tttgagcatg agagtgaaga cagggtagaa gcttcaaacc tcatgatgac cccaataact   300
gttatgagac acatcgttga tttctggaat ctccaagatg ttgccacaca tccagcattc   360
ccttcatctt cattatctga dacagaaatg ccaaggatag ttgatactca aggattctgc   420
gtgggtctgc ttgcagcaat tgcggtggcc tgctctcgaa acacacagga gttccaatat   480
gtggcgtcaa atgccatacg ccttcctctt tgcgttggag cgctagtgga cttggatgag   540
attttgtgtg gctcaaccac gtcactggca gtcaggtggg agtccgtaga ggacttcaac   600
catctcgaaa aaatcctaaa caacaaccct gaaggataca catcatgcta cacagacgtc   660
aaaagtgtca ctatcactat ccccaatgac agcgcagaac gagtgaagca ggagatccat   720
gatcatgggc ttcgtacaaa gcaactttcc ctccagggc gattccatca tgaggcacac    780
cgcgagggaa tccaacacat catgaagtta tgcacgaatg attctcgttt caagcttcct    840
```

```
cgaagtgatg ccttattaac tccgcttcgg tcgagccagg gcggggagat attccaacaa    900
gaagcattac tacacactgt tgcactggac tcaattcttt gtgccaaagc aaactggtac    960
gacgttgtct ccgctttgat caacagcaca gaaatgacag ttgatcaatc tcacctactg   1020
tctattggac ccgaggagtt cgttccacgg tctgcgagga gtaggtcggt ggcacgaaga   1080
gaacttcaga gctacgcaat gcaaggattt tccaacgaaa gcccacagcc ctccacggcg   1140
tccttgtcaa actctgtgca gaccttcgac tctcgtccgc aggcggctga ggcgtcgccc   1200
atcgccatca ccggcatggc atgtcggtat cccaacgcag acacactcgc tcagctgtgg   1260
gatctacttg agttaggtcg gtgcacagtg aagtcgcccc ctgagagccg attccatatg   1320
tccgacttgc aacgcgagcc caaaggccca ttctggggtc acttcctgga gcgcccagac   1380
gtctttgacc atcgcttttt caatatttcg gctcgggaag ccgaatccat ggatcccag    1440 cagcgcgtcg cgctgcaggt agcatacgaa gccatgagt ctgctggata cttaggatgg    1500
cagccaaacg gactctcacg ggatattggg tgttacgtcg gtgtcggatc tgaagattat   1560
acagagaatg tggcatcaag gaacgcgaat gcgttctcca tcacgggaac cctgcagtcg   1620
ttcattgcag gcggatcag ccatcacttc ggctggtcag gccctcaat cagcttggac    1680 acagcgtgct catcggcggc agtggctatt catctggcat gcaaagctct gcaaacaaat   1740
gattgcaaga tcgctttggc cggtggtgtg aatgttttga caaacccag agtgtaccag    1800 aacctgagtg ctgcgtcttt cctgtcacca agcggagcat gcaagccctt gacgcttct    1860 gccgatggat actgccgcgg agagggcgcc gggttattcg ttctgcgacc cttgcaggat   1920
gcaattgaca acggagatcc aattctcggt gtgatcgctg gatcagctgt caaccagggc   1980
tccaacaatt caccaatcac agtccccgat gcggaagccc aacggtcact ctataacaag   2040
gctatgtcgc tcgctggagt ttcccctgac gaggtcacct atgtggaagc ccatggcact   2100
ggcacccaag tcggggatcc cattgagctg acagccttc ggagaacatt tggtggccct    2160
caacgcagaa acagcctcca catcggatcg atcaaggaa atatcgggca tactgagaca    2220
tcctctgggg ccgcgggtct gctgaagacc atccttatgc tccaacaaca acgcatcccg   2280
agacaggcaa acttcaatca gttgaatccc aaggtcaagt ctctcacacc cgaccggttg   2340
gtgatcgctt cagagtcgac tgaatgggca tcgaccgagc gcgttgccat ggtcagcaac   2400 tacgggcat cgggaagcaa cgcagcgctc atagtgaagg agcacgctcc catccgctcc    2460
gagcaaaacg gaacagcccc tgagtatatc caaaatgtgc caatcttggt ctccgctcgg   2520
tctgaagaat ccctccgggc ttactgcggt gcccttcgcg cgaccctttt gagccaccca   2580
ccatctgaaa ctctggtgca gaagttggca tacaacctcg cgatgaagca aaaccgagac   2640
cttccactca atctcacttt tcaacttct tcggacgcca cctcgctgag cgcccgactt    2700
gaggccattt ccacgggcgc atccgccgat ctgattcaga agcggccttc caatgagccc   2760
ccagttgttt tgtgtttcgg tggtcaaaat ggacttacgg caaccatttc gaaggaagtt   2820
ttcgacgcct ccgctcttct acggacccac ctcgaagatt gcgaggaagt gggccgaacg   2880
cttggccttc ccagtctttt cccaactatc ttcagctcag ccccgatcac aaacatcatc   2940
catttgcatt tcatactctt ctctattcag tatgcttctg caaaggcatg gctggactct   3000
ggacttcgtg tcagtcgcat tgtgggacac agctttggtc agttgactgc tttgtctgtg   3060
gcgggcagct tgagcgttcg cgatggcatt cacctagtca ctgagcgtgc tcgcctcatt   3120
gagtccagct ggggcccaga atctgggatc atgctcgccg ttgaagggac ggacattgag   3180
gtccaacagc tgctagacca gacgggtcat atcgctgacg ttgcctgcta caatgggcca   3240
```

```
cgacagcaag tactggcagg tacagcggaa tctatcgcgg cgattgagaa cgccgctgct    3300
agaaccccat ctgcatcaaa gttgcggttg actcggctgc aaaattccca tgctttccat    3360
tctcgacttg tcgatagcat tgtgcccgcc atcatggagg tggctgggtc ccttgtttac    3420
cagacaccga tcattcccat cgaagcctgc tctgcaagtg gtgactggtc aaccatcaca    3480
gcggctgaga ttgtggagca cagccgcatg cctgtgtact tccgacgtgc tgttgagcga    3540
gtagctgaaa agctacaagc ccccgccgtc tggctggaag caggatccgc ttcacccatc    3600
ataccaatgg tacgccgagt gctagagagc tcttcggttg ccaacacata ccacaaaatt    3660
gacttgggtg gttcaagtgg agcccaaaat ttggcaaacg tcactagcgc cctctgggca    3720
cagggtgtac atgttcagtt ctggcctttc gatcgggccc agcatggaag cttcaaatgg    3780
atgaaccttc caccatatca gtttgcccaa aacagccact gggttgactt tgaccctgca    3840
gcgttttcat ctgctggacc ttcgtctgga aagcagtccg caggacaaga agcaggtctt    3900
ctgtgtcaat tgagcgagag cccagatgag cgtctctatc atgttaacat tcaagatgcc    3960
ctctacagag catgcaccca gggacacgca gttctgaatc agacattgtg tcccgcctcc    4020
atgtacatgg agatggtttt gcgggcagca gcctccattt tccccacggg caacgcttct    4080
gagccagcca tgtcacatat cgaggatctg accatctcct cgcccttggt attggaccca    4140
caaggagatg tgttcctgag actcaccagc gatggagcgg gtcctactcg accatggctc    4200
ttttcgatct tcagcagtga gtcaaatgat catacatcgg tccacgctga aggtaccgtg    4260
tgtcttcatc aggagcgttc tagggctctg gcgcgcttcc agtccatgga tcgactgttg    4320
gactcggcac gaagcaaaac cattgaagcg gaccctgctt caaacgggct gaagggctct    4380
actgtctatg ctgctcttga atctgtaacc aactatggag actacttccg tggcgtgaag    4440
aaagtatttg caaacggtcg ggaagccagt ggtctggtat ccatgatgcc atcagccagt    4500
gagaccaact gcgaccctat tctgctagac aacttcctcc aagttgctgg aattcacgtc    4560
aactgccttt ctgatcgccg gtcaagcgaa gtctttgtct gcaacgctat tggggagaca    4620
tttgttatca actccttgct caagcaaaag aatggcgctt ctccttcgac atggaaggtg    4680
tacaccagct acgtccggcc gtctaagact gagatcgcat gtgacatcta tgtgatggac    4740
tgccaaacag atacactctc tgcggcaatg atgggtgttc gatttacgag cgtctcaatc    4800
cgctctctca cccgcgcgct ggccaagctg aacaacaatg tcctagagac cgctgaagcc    4860
caatcagttg tggagcctgc gattccggct gagaaatcag ttgtgacagc cactcctagt    4920
gcgccggctg ccgatggagg tggggctaaa gatcttgcca ctgtccagga gatgctctgt    4980
gagctctttg gagtcagtgt cgcggaggtc tctccttcag tgtcgctggt agacattggg    5040
gtggactctc tcatgagcac tgaagttctt tctgaaatca gaagaggtt ccaagtcgat    5100 atgtcgtata ccactttggt ggacatcccc aacattcaag gtctggtgga acatatcttc    5160
cccggacatt ctcacgctgc cccctcacag cctgttgttg aaacagcgcc agtacagtcg    5220
gtggcaccac aagctgtatc ccatgtaccg acaccggcta acaatggacc accactagtc    5280
tcagtggccc gccagtgctt tgacacaacg cacgcagcgg tatctcacac ctccgatgct    5340
cactggactg gcttcttcca caccacctac ccgaaacaaa tgacacttct tactgcctac    5400
atcctcgagg cattccgagc tttgggctct ccgctggagg cgagtgaacc aaacgaagtt    5460
ctcatcccca tctctgtgct accacgtcac gagcaactcc gaaagcatct ttacaagatc    5520
ttggagtcag tcggtttggt ccgccagatg cccactgggg agcttgtgcg cacaacaaca    5580
cccatcccgt tgtcgcagtc gcatgacctg cacacgcaga taagagcgga atatcctcca    5640
```

| | | | | |
|---|---|---|---|---|
| tatgccctgg | agcatgatct | tcttcaaatc | acagcccctc | ggctcgctga ctgtctcact | 5700 |
| ggaaaagcgg | acggagtatc | tctgatattc | caggatgcga | acacacggcg cttggtgggc | 5760 |
| gatgtgtacg | cgcaatctcc | ggttttcaaa | tcgggcaacc | tctatcttgc tcgttacctt | 5820 |
| ttagatgttg | ttcaatcatt | tggaagcagc | cggactatca | agatccttga gattggtgcc | 5880 |
| ggtacaggag | gtactaccaa | gaatctcctc | gagaagctgt | ccacaattcc tggactgtcc | 5940 |
| acgcgcctgg | agtacacatt | cacagatatc | tcaccatcac | ttgttgcagc tgggcggaag | 6000 |
| acctttgcta | actacaattt | catgcgatat | gaaactctga | atgttgaaaa tgaccctccc | 6060 |
| tcagctttga | gtggtcaata | tgatatcgtg | cttcgacca | attgtgtcca tgccacccgc | 6120 |
| aacctccggg | aatcttgcac | taacattcgc | aagcttttga | gacctgatgg aatcttgtgt | 6180 |
| cttgtcgagc | tgacccgtga | catcttctgg | ttggatcttg | tctttggtct cctggaaggc | 6240 |
| tggtggcgat | tcgaagacgg | acgtgaacac | gcgctggcta | ctgagatgat gtgggatcag | 6300 |
| actcttcgtc | aatctggatt | tgagtgggtt | gactggacaa | acaatgagac cgtagagtca | 6360 |
| aatgctctgc | gtgtcattgt | cgcttcgccg | acaggaaact | catccaccgc gacaatgtct | 6420 |
| ccatcgaaac | tcacaaagat | ggaaaccgtg | gtttggggtg | agcagacaa tctgcagctc | 6480 |
| cgtgcagaca | tctactatcc | cgagaccgtg | gacactactc | ggaagcagcg accgattgcc | 6540 |
| ctgatgatcc | acgaggtgg | ccacgtcatg | ctatctcgca | aggacatccg tccagcccag | 6600 |
| actcagaccc | ttctggatgc | cggcttcctg | cctgttagca | tcgactaccg cttgtgccca | 6660 |
| gaagtttcac | tagcagaagg | cccaatggcc | gatgcccgcg | acgctctgtc ctgggttcgc | 6720 |
| cgcgtcctcc | cgaatattcc | cttgctgcgc | gcagatattc | gacccgacgg gaaccaggtc | 6780 |
| gtggctatcg | gatggtctac | tggtggtcat | ctcgccatga | cgctaccttt cacggcccca | 6840 |
| gctgctggta | tttcagctcc | aaacgccgtc | ttggcattct | actgcccgac caactacgag | 6900 |
| gatccattct | ggtcgaaccc | aaatttcccc | ttcgggcaga | cagtcgcatc gaacgagatg | 6960 |
| gagtacgatg | tttgggaagg | attgcagagc | atgccgatag | ccggctacaa ccctgcactc | 7020 |
| aaggaacgcc | ctctcggggg | ctggatgtca | acgagagatc | cgcgcagtcg gatcgcactg | 7080 |
| cacatgaact | ggactggaca | aaccttgcct | gttctgttaa | aggcatgcac aatcaagggt | 7140 |
| aacaccgaga | aatgcagccc | cgatgaccta | tctcgtccga | cagaggagga gattcaggca | 7200 |
| gtcagtccca | attatcagat | ccgcgtcggt | cgctacaaca | cgccgacatt cttgattcat | 7260 |
| ggaacaagtg | atgaccttgt | tccttgtgct | caaacggagt | ccacgcatgg tgcattgacg | 7320 |
| gccagcggag | tcgaggcgga | gcttagagtg | gtgcaggaag | ctgcacacct tttcgacctt | 7380 |
| tacccagcct | cacacgctgg | ccaggaagcg | aaggccgcag | tggcggaagg atatgagttc | 7440 |
| ttgagaagac | atgttcagct | t | | | 7461 |

<210> SEQ ID NO 12
<211> LENGTH: 1605
<212> TYPE: DNA
<213> ORGANISM: Penicillium brevicompactum

<400> SEQUENCE: 12

| | | | | |
|---|---|---|---|---|
| atgaagtctt | tgtcgctaac | atggatcacg | gctgttgccg | tggtactata tctcgtccaa | 60 |
| cgctatgtca | ggtcatattg | gcggctcaag | gatataccag | gtccggtgtt ggcaaaactc | 120 |
| acagatctcc | aacgtgtgtg | gtgggtgaag | actggccgag | cacatgagtt tcatcgtgac | 180 |
| atgcatgcca | tgtatggccc | tatcgttcga | tttggaccaa | acatggtttc agtctctgat | 240 |
| cctcgtgtta | taccgaccat | ctacccaagt | agacctggat | tcccgaaggg tgacttctat | 300 |

```
cgcacgcaaa agccatacac ccggaataag ggcgcaatgc ccgcggtctt caacactcaa    360
gacgaggatc tgcacaagca acttcgaagc ccgatcgcct cgttatattc catgacaaat    420
gtggtgagac tcgagccact ggttgatgaa actcttacag tactatcgaa acaactcgat    480
gagcgcttcg tgggtacgaa tgataagccg ttcgatctcg gggactggtt gcaatatttc    540
gccttcgact ccatgggcac attgactttc tcgcgaagat acggcttttt ggaacaaggt    600
cgtgatatgc atggaatctt gcaggagatt tggaatttta tgacccgagt cgctgtgatg    660
ggacaaattc cgtggtttga cgagatctgg aataagaatt cgttcattac tttattcaag    720
cgacctaccg gctttggtgt gttgaaggtt gtcgataact ttatatctca acgagtgtcc    780
agtcgtgaga tgacgagaa agcagacgaa aagacatgc tttctcagtt cttggacatc    840
caagcatcaa atcctcactc tatcatgcct tgggcaccaa gagcgtggac cttctctaat    900
gtcatggctg gctcagactc tactgcgaat gtcatgcgta ccatgatgta caaccttctc    960
gttgaccgag atacgttgag aagtctgcga gccgagcttt tggaagcgga gaactcaaat   1020
ggcctgtctc gatccttgcc ttcttgggat ggagtgagaa gcttgcctta ccttgatgca   1080
tgcgttctcg aagctttgcg tctgcatccc ccattctgtc tgccctttga acgagtcgtc   1140
cctgaaggcg gtatacagt ctgtgagaca tatcttccag cgggaacagt tgttggaatt   1200
agtccctact tggccaaccg cgataaacaa acctttggtg atgacgcaga taatgcga    1260 cccagcagat ggttagattt gagccgcgaa gatcgggtca aacttgagaa cagtattctc   1320
acgtttggtg cgggacgtcg gacttgttta ggaaagaaca tcgccattct tgagatcaag   1380
aagctctttc cgatgttgct tttgaattat gaaatcgaaa ttgtgaaccc tgaaaactac   1440
cagaccacaa atgcctggtt tttcagacag tggggcttgc aagcggtgat cgcaaactg   1500 ccagcaccag aacgagatga taccattgag cagaaagctt ccatcccgcc tgctttgaat   1560
attcctcctt catcttcgac agtcgaagtg cgaattattg actcg              1605

<210> SEQ ID NO 13
<211> LENGTH: 783
<212> TYPE: DNA
<213> ORGANISM: Penicillium brevicompactum

<400> SEQUENCE: 13
atgatcaaat cgcaaacggt catccaagag ccacgcaaca tctcagatgt tcttgactca     60
gacgaatcct ctctgggggt ccggagcaaa gatattgaag cgattatctg gtcacatgcc    120
cattttgacc acattggtga cccatcaact ttcccccccgt ctaccgagct agtcgtcgga    180
cctggcatcc gagacaccca ctggcccggc ttcccaacta acccagacgc aatcaacctc    240
aacaccgaca tccaaggtcg caatgtgcga gaaatttcct tcgaaaagac acagaaggga    300
gccaccaaga tcggttcttt cgacgccgtg gactatttg gcgatgggtc ctttttatctt    360 ctagatgctg cgggtcattc cgtgggccat atcggtgctc ttgctcgcgt gactacctct    420
ccagtctcgt ttgtcttcat gggtggtgac tcatgtcacc atgccggagt gcttcgaccc    480
acaaaatatc ttccttgtcc acttgactct ggtgacactc acttccatg caaatccgac    540 tctgttttca cgttatcgcc tgcactgcca actgattaca ctgctgcttt gaggacagtc    600
gagaatatta aggagctcga tgcctgtgag atgtattcg tcgtccttgc tcatgatgct    660
accttgaaag gaaggtcga cttttacccct tcgaaaatca atgattggaa ggcgaaagag    720
tacggcaaga agacaaagtg gcttttttac aaggatattg agaattccat agaaggacag    780
aag                                                                 783
```

-continued

<210> SEQ ID NO 14
<211> LENGTH: 1581
<212> TYPE: DNA
<213> ORGANISM: Penicillium brevicompactum

<400> SEQUENCE: 14

| | | | | | |
|---|---|---|---|---|---|
| atggtcgaaa | tcctggacta | caccaaggcc | ttggaggtcc | tgaaggagta | tccttccgga | 60 |
| gatggtctcc | atgtcgatac | ccttctcgac | tccgacaacc | acggagcctt | gacctacaat | 120 |
| gacttcctca | tcctgcccgg | ctctatcact | ttctcagcag | cggacgtttc | tttggatacc | 180 |
| aaggtgaccc | ggcggttcac | catcaaggcc | ccactcctct | cgtcccccat | ggacacggtg | 240 |
| accgaacata | acatggctat | tcacatggct | cttctgggcg | gtctgggagt | tattcacaac | 300 |
| aactgcccac | ccgatgacca | agctgagatg | gtcaggaagg | tgaagcgcta | tgagaacggc | 360 |
| ttcatcctcg | accccgtcgt | tctgtcccct | agcacaaccg | tcgcagaggc | aaaggaattg | 420 |
| aagaccaaat | ggaacttcgg | cggattccca | gtgaccgaga | agggcactct | ccactccaag | 480 |
| cttctcggca | tcgtcactag | cagagatatc | cagttccaca | agactccaga | ggatccagtc | 540 |
| acagccgtta | tgtcgactga | ccttgtcacc | gcacccgcgg | aaccacccct | ggctgaagcc | 600 |
| aatgaagtcc | tccgcagctc | caagaagggc | aagcttccca | ttgtggacaa | ggacggatta | 660 |
| ttggtctccc | tcctctctcg | cagtgatctg | atgaagaata | tccactatcc | cctcgcatcc | 720 |
| aagcttccat | ccaagcagct | gctctgcgct | gcggctatca | gcacccacga | cgctgacaag | 780 |
| gtccgccttc | agaagctcgt | cgacgctggt | ctcgacattg | tcgttgtgga | cagcagccag | 840 |
| ggaaacagca | tgtaccagat | tgctatgatt | aagtggatca | agtctacctt | cccagacatc | 900 |
| gatatcatcg | ccggtaacat | cgttacccgt | gagcaggccg | ccgcactgat | tgccgctggt | 960 |
| gccgacggtc | tgcgtatcgg | tatgggcagt | ggctccgcat | gcattaccca | agaagtcatg | 1020 |
| gccgtcggtc | gcccccaggc | tgcttccgtc | cgcagtgttt | ctgccttcgc | cgcccgtttc | 1080 |
| ggcgttccta | ctatcgccga | cggcggtgtc | cagaacctgg | acacattgt | caagggcctt | 1140 |
| gcacttggtg | cctccgcagt | tatgatggga | agcttgcttg | ccggtactac | cgagtctcct | 1200 |
| ggcgagtact | acgttagcaa | tgaaggtcag | ctggtcaagg | ccttccgcgg | tatgggtagt | 1260 |
| atcgctgtta | tggaggacaa | gggcaagagt | ggtggcggca | agaacgctgg | cgcttcccgc | 1320 |
| tacttctctg | agaacgacaa | ggtcaaggtc | gcccagggtg | ttgcgggctc | tgtcgtcgac | 1380 |
| cgcggttcca | tcacgcaata | cgtgccttac | cttgttgctg | gtattcagca | ctctctccag | 1440 |
| gatatcggtg | ttcaggatct | tgaggccctg | cacaccggtg | tgaacaacgg | acaggttcgc | 1500 |
| tttgagatga | agcgccag | cgcgcagacc | gagggcaatg | ttcacggtct | tcacagccac | 1560 |
| gagaagaagt | tgtactcttc | t | | | | 1581 |

<210> SEQ ID NO 15
<211> LENGTH: 1194
<212> TYPE: DNA
<213> ORGANISM: Penicillium brevicompactum

<400> SEQUENCE: 15

| | | | | | |
|---|---|---|---|---|---|
| atgagtgccg | catcccagc | ctccattatc | caggagcttg | cgtcggcagc | caaacaatac | 60 |
| gagaacaatg | aatctggtgc | aagggaagct | ctcattgctc | agagcagagc | cttgattgcc | 120 |
| tcacttgaag | ttccaagcga | gttcatccaa | cacaccttct | ggtctcagcc | cgcccttcct | 180 |
| gctatcgtca | gacttgctac | cgatgtaaac | cttttccaat | acctgaaaga | tgcccaagaa | 240 |
| gagggtttga | gcgccgaagc | tctggcctca | aagactggca | tggatgtgag | cctttcgca | 300 |

```
cgcttggcca gacatcttgt ggccatgaac gtgatcactt cccgcaacgg agtgttctat    360
ggcacagcct tgagcaacgg ccttgccgct gaaaactatc aacaatcaat ccgcttctgt    420
catgatgtgt ccaggccctc gttcggtgcc ttcccgagct ttttcaaagg caatgggtac    480
aagacccctg ccctgggcac cactgatggc ccattccaat ctgcacacaa ggttgacatt    540
tcattcccac aatggcttgt cggaaatccc ccttacctgc aatacttcaa ctcttacatg    600
agtgcctacc gcgctggaaa gccgaactgg tgtgacaacg gcttttaccc tgtcgcagac    660
cgtcttctga tgggtttga cgcctctgtg agcgatgttc tgctggtcga cgtcggcggt    720
ggtcgtggtc atgacatcgc caccttcggc tctcaattca gtccgctccc aggaagactt    780
gttcttcaag atcgagaaca ggtcatcaac agcatcccg ctgatgagtc ccgtcaattt    840
gaagcgacga cccatgacat cttcacaacg cagcccgtga agaatgctcg ggcttactac    900
atgcactccg ttcctcacgg cttcggagac gaggatgcag ttaagatcat ggccaacctt    960
gttcctgctt tggcgaaggg ttactcccgt gtgctcctca atgagattgt tgttgacgag   1020
gagagcccag tgatgtcagc gaccaacatg gacttgatca tgctggccca catggggcc   1080 aaggagagaa cagaggccga ttggagatcc attctgaccc gggccgggtt gaaggtagtc   1140
aacatatact cgtatcccgg cgtggcagag agtttgattg aagcggaact cgcc         1194
```

<210> SEQ ID NO 16
<211> LENGTH: 1302
<212> TYPE: DNA
<213> ORGANISM: Penicillium brevicompactum

<400> SEQUENCE: 16

```
atgtcaactg agaaatttac catcactgag cacctggtcc caggcagcca tattagggaa     60
tatcccggaa gtacggttaa ccagcaggat gttttgaaga ttcatgtcaa aaattatact    120
cctaaacgag agggtccggt tccagacgat gcaatcactt tcattgccac tcacggagtc    180
ggtctgccaa aggagctgta tgagccacta tgggatgagc tcctagacca agcttctgga    240
tttcatatcc gtgccatatg gatggccgat gtcgccagca tgaatcagag tggcattcac    300
aatgaagaca agctcagcat ggattgctcc tggatggatc atgcccgaga ccttttgttg    360
atgatcaacc atttccggga ccagatgcca cgtcctctag ttggaatcgg ccacagcttt    420
ggtggcaata ttatcaccaa ccttgcctac ttgcatcccc gtcttttttac tactctccta    480 ctgctagatc tcttattca gctaagtcca ccctctttgg gctttggaac cgatgctcca    540
agtgcgatca actacactct ctggcgagat gatgtatggc caagccggga agaagcaata    600
cgcgccaacc gcgctatcat gcaaggcatg gatccccgat gcttggatcg catgacgaaa    660
cacttctttc gcgatctacc aaccccactc tacccagatg ttgaggccat aaaggctcgc    720
tttggaacca ctgcggactc tactaccact ccagtcactt tgacgacacc aaaatatcat    780
gagctcgtag ctcaaattcg acaaaacttc aatgcccgtg acccgaagac aggtcgcatt    840
gaagttccgc gcgacactca tgccgacatg gatccactgg ttgcttatat tccattgtac    900
cgcccggaac cccgaagcac attccgtcgt ctggagacgc ttcgaccgtc atgcttatgg    960
gtcatagccg cgctacgtt tttgaacatc gatgagatac gcgaaggtgt caagatatgc   1020
ggatcaggta ttggtgggag cggaggtgtg ccggatggga gggttcgcga ggttgttctt   1080
ccagggtttg ggcatttgat gccattccaa gaagtgaaga ccgttgcagg aacatgtgtg   1140
gtctggcttc agcaggagat ggatcgattc cgtcagactg aaagacagtg gaaagaagac   1200
agggatggga aaagtcatca ggcggttgaa gaaaattggt ataaggtttt gaagccaatt   1260
```

```
cctactggac gcaagaagag gagtgataag ggaaaacttt ag                           1302
```

<210> SEQ ID NO 17
<211> LENGTH: 8
<212> TYPE: PRT
<213> ORGANISM: Artificial Sequence
<220> FEATURE:
<223> OTHER INFORMATION: Primer - protein sequence

<400> SEQUENCE: 17

```
Gly Gly Leu Thr Tyr Asn Asp Phe
1               5
```

<210> SEQ ID NO 18
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (3)..(3)
<223> OTHER INFORMATION: n = I (inosine)
<220> FEATURE:
<221> NAME/KEY: modified_base
<222> LOCATION: (6)..(6)
<223> OTHER INFORMATION: n = I (inosine)
<220> FEATURE:
<221> NAME/KEY: modified_base
<222> LOCATION: (7)..(7)
<223> OTHER INFORMATION: y = t or c
<220> FEATURE:
<221> NAME/KEY: modified_base
<222> LOCATION: (9)..(9)
<223> OTHER INFORMATION: n = I (inosine)
<220> FEATURE:
<221> NAME/KEY: modified_base
<222> LOCATION: (15)..(15)
<223> OTHER INFORMATION: y = t or c
<220> FEATURE:
<221> NAME/KEY: modified_base
<222> LOCATION: (18)..(18)
<223> OTHER INFORMATION: y = t or c
<220> FEATURE:
<221> NAME/KEY: modified_base
<222> LOCATION: (21)..(21)
<223> OTHER INFORMATION: y = t or c

<400> SEQUENCE: 18

```
ggnggnytna cttayaayga yttc                                              24
```

<210> SEQ ID NO 19
<211> LENGTH: 10
<212> TYPE: PRT
<213> ORGANISM: Artificial Sequence
<220> FEATURE:
<223> OTHER INFORMATION: primer protein seq

<400> SEQUENCE: 19

```
Gly Asn Val Val Thr Arg Glu Gln Ala Ala
1               5                   10
```

<210> SEQ ID NO 20
<211> LENGTH: 28
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (3)..(3)
<223> OTHER INFORMATION: n = I (Inosine)

```
<220> FEATURE:
<221> NAME/KEY: modified_base
<222> LOCATION: (6)..(6)
<223> OTHER INFORMATION: y = t or c
<220> FEATURE:
<221> NAME/KEY: modified_base
<222> LOCATION: (9)..(9)
<223> OTHER INFORMATION: y = t or c
<220> FEATURE:
<221> NAME/KEY: modified_base
<222> LOCATION: (12)..(12)
<223> OTHER INFORMATION: n=I (Inosine)
<220> FEATURE:
<221> NAME/KEY: modified_base
<222> LOCATION: (15)..(15)
<223> OTHER INFORMATION: n=I (inosine)
<220> FEATURE:
<221> NAME/KEY: modified_base
<222> LOCATION: (18)..(18)
<223> OTHER INFORMATION: n=I (inosine)
<220> FEATURE:
<221> NAME/KEY: modified_base
<222> LOCATION: (21)..(21)
<223> OTHER INFORMATION: n=I (inosine)

<400> SEQUENCE: 20
gcngcytgyt cnckngtnac nacrttcc                                    28

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
gaggtgaccg ctacgtgtgt                                             20

<210> SEQ ID NO 22
<211> LENGTH: 40
<212> TYPE: DNA
<213> ORGANISM: Artificial Sequence
<220> FEATURE:
<223> OTHER INFORMATION: Primer

<400> SEQUENCE: 22
gatccccggg aattgccatg cgtgctgcga tactcattgc                       40

<210> SEQ ID NO 23
<211> LENGTH: 40
<212> TYPE: DNA
<213> ORGANISM: Artificial Sequence
<220> FEATURE:
<223> OTHER INFORMATION: Primer

<400> SEQUENCE: 23
ggactgagta gcctgacatc ggtcgtaagc cttggctgtg                       40

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
cctacgcggt ttcctgagtt                                             20

<210> SEQ ID NO 25
<211> LENGTH: 43
```

```
<212> TYPE: DNA
<213> ORGANISM: Artificial Sequence
<220> FEATURE:
<223> OTHER INFORMATION: Primer

<400> SEQUENCE: 25
catggcaatt cccggggatc gctgattctg gagtgaccca gag          43

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26
ctgctgctcc atacaagcca acc                                23

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27
gacattgggg aattcagcga gag                                23

<210> SEQ ID NO 28
<211> LENGTH: 43
<212> TYPE: DNA
<213> ORGANISM: Artificial Sequence
<220> FEATURE:
<223> OTHER INFORMATION: Primer

<400> SEQUENCE: 28
gatgtcaggc tactcagtcc cgttgtaaaa cgacggccag tgc          43

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
cagacggcag acaaccgaga                                    20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
tgggctcgta tttgactccg                                    20

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
ggacacacgt aggcaatgag t                                  21
```

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ggtggcacca caagctgtat                                        20

<210> SEQ ID NO 33
<211> LENGTH: 9
<212> TYPE: PRT
<213> ORGANISM: Penicillium brevicompactum

<400> SEQUENCE: 33

Ile Leu Glu Ile Gly Ala Gly Thr Gly
1               5

<210> SEQ ID NO 34
<211> LENGTH: 8
<212> TYPE: PRT
<213> ORGANISM: Penicillium brevicompactum

<400> SEQUENCE: 34

Gly Gln Tyr Asp Ile Val Leu Ser
1               5

<210> SEQ ID NO 35
<211> LENGTH: 9
<212> TYPE: PRT
<213> ORGANISM: Penicillium brevicompactum

<400> SEQUENCE: 35

Leu Leu Arg Pro Asp Gly Ile Leu Cys
1               5

<210> SEQ ID NO 36
<211> LENGTH: 36
<212> TYPE: PRT
<213> ORGANISM: Artificial Sequence
<220> FEATURE:
<223> OTHER INFORMATION: Consensus pattern
<220> FEATURE:
<221> NAME/KEY: VARIANT
<222> LOCATION: (2)..(4)
<223> OTHER INFORMATION: Xaa Xaa Xaa= Any three amino acid residues
<220> FEATURE:
<221> NAME/KEY: VARIANT
<222> LOCATION: (8)..(9)
<223> OTHER INFORMATION: Xaa Xaa= Any two amino acid residues
<220> FEATURE:
<221> NAME/KEY: VARIANT
<222> LOCATION: (17)..(18)
<223> OTHER INFORMATION: Xaa Xaa= Any two amino acid residues
<220> FEATURE:
<221> NAME/KEY: VARIANT
<222> LOCATION: (21)..(21)
<223> OTHER INFORMATION: Xaa = Any amino acid residue
<220> FEATURE:
<221> NAME/KEY: VARIANT
<222> LOCATION: (25)..(26)
<223> OTHER INFORMATION: Xaa Xaa = Any two amino acid residues
<220> FEATURE:
<221> NAME/KEY: VARIANT
<222> LOCATION: (28)..(31)
<223> OTHER INFORMATION: Xaa Xaa Xaa Xaa = Any four amino acid residues

<400> SEQUENCE: 36

```
Asn Xaa Xaa Xaa Asp Glu His Xaa Xaa Leu Ile Met Phe Tyr Thr Asp
1               5               10              15

Xaa Xaa Val Met Xaa Arg Ser Thr Xaa Xaa Arg Xaa Xaa Xaa Xaa Gly
            20              25              30

Tyr Asn Lys Arg
        35

<210> SEQ ID NO 37
<211> LENGTH: 19
<212> TYPE: PRT
<213> ORGANISM: Artificial Sequence
<220> FEATURE:
<223> OTHER INFORMATION: Myristoylation sire consensus pattern
<220> FEATURE:
<221> NAME/KEY: VARIANT
<222> LOCATION: (11)..(12)
<223> OTHER INFORMATION: Xaa Xaa = Any two amino acid residues

<400> SEQUENCE: 37

Gly Glu Asp Arg Lys His Pro Phe Tyr Trp Xaa Xaa Ser Thr Ala Gly
1               5               10              15

Cys Asn Pro

<210> SEQ ID NO 38
<211> LENGTH: 6
<212> TYPE: PRT
<213> ORGANISM: Penicillium brevicompactum

<400> SEQUENCE: 38

Gly Ala Gly Asn Thr Trp
1               5

<210> SEQ ID NO 39
<211> LENGTH: 6
<212> TYPE: PRT
<213> ORGANISM: Penicillium brevicompactum

<400> SEQUENCE: 39

Gly Asn Thr Trp Asn Asp
1               5

<210> SEQ ID NO 40
<211> LENGTH: 6
<212> TYPE: PRT
<213> ORGANISM: Penicillium brevicompactum

<400> SEQUENCE: 40

Gly Leu Ala Ile Gly Tyr
1               5
```